(12) United States Patent
Lopez-Hilfiker et al.

(10) Patent No.: US 12,665,180 B2
(45) Date of Patent: Jun. 23, 2026

(54) ION MOLECULE REACTOR AND SETUP FOR ANALYZING COMPLEX MIXTURES

(71) Applicant: TOFWERK AG, Thun (CH)

(72) Inventors: Felipe Lopez-Hilfiker, Bern (CH); Manuel Hutterli, Bern (CH); Marc Gonin, Thun (CH); Carsten Stoermer, Thun (CH); Michael Kamrath, Thun (CH)

(73) Assignee: TOFWERK AG, Thun (CH)

( * ) Notice: Subject to any disclaimer, the term of this patent is extended or adjusted under 35 U.S.C. 154(b) by 17 days.

(21) Appl. No.: 18/410,708

(22) Filed: Jan. 11, 2024

(65) Prior Publication Data

US 2024/0194470 A1     Jun. 13, 2024

Related U.S. Application Data

(62) Division of application No. 16/757,149, filed as application No. PCT/EP2018/078776 on Oct. 19, 2018, now Pat. No. 11,908,673.

(30) Foreign Application Priority Data

Oct. 20, 2017   (EP) ..................................... 17197558
Apr. 25, 2018   (WO) ................. PCT/EP2018/060627

(51) Int. Cl.
*H01J 49/04*       (2006.01)
*G01N 1/22*        (2006.01)
(Continued)

(52) U.S. Cl.
CPC .......... *H01J 49/049* (2013.01); *G01N 1/2226* (2013.01); *G01N 33/46* (2013.01); (Continued)

(58) Field of Classification Search
CPC ........ H01J 49/049; H01J 49/06; H01J 49/062; H01J 49/142; G01N 1/2226; G01N 33/46; G01N 2001/2229
See application file for complete search history.

(56) References Cited

U.S. PATENT DOCUMENTS 3,588,593 A    6/1971   Rabinowitz et al.
4,267,007 A    5/1981   Kellogg
(Continued)

FOREIGN PATENT DOCUMENTS

CA         2 837 478 C      2/2019
CN         101855700 A     10/2010
(Continued)

OTHER PUBLICATIONS

Hearn and Smith, "A Chemical Ionization Mass Spectrometry Method for the Online Analysis of Organic Aerosols", Analytical Chemistry, 2004, 76, 10, 2820-2826 (Year: 2004).*
(Continued)

*Primary Examiner* — David E Smith
(74) *Attorney, Agent, or Firm* — Birch, Stewart, Kolasch & Birch, LLP

(57)        ABSTRACT

An ion molecule reactor for generating analyte ions from analytes comprises:
  a) a reaction volume in which reagent ions can interact with the analytes in order to form analyte ions;
  b) at least one analyte inlet for introducing the analytes along an inlet path into the reaction volume whereby, preferably, the inlet path runs essentially along at least a first section of the predefined transit path in the reaction volume;
  c) at least one reagent ion source and/or at least one reagent ion inlet for providing reagent ions into the reaction volume;

(Continued)

d) optionally, at least one ion guide comprising an electrode arrangement which is configured for producing an alternating electrical, magnetic and/or electromagnetic field, that allows for guiding the reagent ions and/or the analyte ions at least along a section of the predefined transit path, preferably along the whole transit path, through the reaction volume.

23 Claims, 12 Drawing Sheets

(51) Int. Cl.
    *G01N 33/46*     (2006.01)
    *H01J 49/06*     (2006.01)
    *H01J 49/14*     (2006.01)

(52) U.S. Cl.
    CPC .......... *H01J 49/062* (2013.01); *H01J 49/145* (2013.01); *G01N 2001/2229* (2013.01)

(56)         References Cited

U.S. PATENT DOCUMENTS

| | | | |
|---|---|---|---|
| 4,975,576 A | 12/1990 | Federer et al. | |
| 5,175,431 A | 12/1992 | Eisele et al. | |
| 5,441,700 A | 8/1995 | Markelov | |
| 5,646,334 A | 7/1997 | Scheppers et al. | |
| 5,856,674 A | 1/1999 | Kellerman | |
| 5,969,352 A * | 10/1999 | French | H01J 49/105 |
| | | | 250/288 |
| 6,119,534 A | 9/2000 | Dinsmore | |
| 9,588,089 B2 * | 3/2017 | Riboulet | G01N 30/7206 |
| 2003/0111600 A1 | 6/2003 | Thomson et al. | |
| 2008/0217528 A1 * | 9/2008 | Gonin | H01J 49/04 |
| | | | 250/287 |
| 2009/0038374 A1 | 2/2009 | Broz | |
| 2013/0026360 A1 * | 1/2013 | Stoermer | H01J 49/0072 |
| | | | 250/292 |
| 2013/0193318 A1 | 8/2013 | Land et al. | |
| 2014/0284204 A1 * | 9/2014 | Sipila | H01J 49/145 |
| | | | 204/157.64 |
| 2014/0331861 A1 | 11/2014 | Makarov et al. | |
| 2017/0241967 A1 | 8/2017 | Silva Ferreira et al. | |
| 2018/0166268 A1 | 6/2018 | Wang et al. | |

FOREIGN PATENT DOCUMENTS

| | | | | |
|---|---|---|---|---|
| CN | 203386713 U | 1/2014 | | |
| CN | 107078717 A | 8/2017 | | |
| DE | 196 28 093 A1 | 1/1998 | | |
| EP | 3327750 A1 * | 5/2018 | | H01J 49/04 |
| WO | WO 2017/013609 A1 | 1/2017 | | |

OTHER PUBLICATIONS

Cacho et al. "Direct sample introduction-gas chromatography-mass spectrometry for the determination of haloanisole compounds in cork stoppers," Journal of Chromatography A, vol. 1475, 2016, pp. 74-79.

Copolovici et al., "Volatile Emissions from Alnus glutionosa Induced by Herbivory are Quantitatively Related to the Extent of Damage," Journal of Chemical Ecology, vol. 37, 2011 (published online Dec. 23, 2010), pp. 18-28.

European Communication pursuant to Article 94(3) EPC for European Application No. 18 786 796.5, dated Jun. 30, 2023.

Lim et al., "Noninvasive Identification of Tainted Corks in Full Intact Wine Bottles: A Low-Pressure Room Temperature Study," American Journal of Enology and Viticulture, vol. 62, No. 3, 2011, pp. 291-297.

Tarasov et al., ""Cork taint" responsible compounds. Determination of haloanisoles and halophenols in cork matrix: A review," Talanta, vol. 175, 2017, pp. 82-92.

\* cited by examiner

ION MOLECULE REACTOR AND SETUP FOR ANALYZING COMPLEX MIXTURES

This application is a Divisional of copending application Ser. No. 16/757,149I, filed on Apr. 17, 2020, which is the National Phase under 35 U.S.C. § 371 of International Application No. PCT/EP2018/078776, filed on Oct. 19, 2018, which claims the benefit under 35 U.S.C. § 119(a) to patent application Ser. No. 17/197,558.4, filed in Europe on Oct. 20, 2017 and PCT/EP2018/060627 filed in Europe on Apr. 25, 2018, all of which are hereby expressly incorporated by reference into the present application.

TECHNICAL FIELD

The invention relates to an ion molecule reactor for generating analyte ions from analytes, in particular for use with a mass spectrometer, as well as corresponding methods for generating analyte ions and for analysing a sample, especially a cork stopper. Further aspects of the invention are concerned with a mass spectrometer, a kit of parts comprising an ion molecule reactor, a setup for analysing a sample and the use of an ion molecule reactor in mass spectrometry, for the analysis of a gaseous mixture comprising at least one analyte and for analyzing a cork stopper for the presence of cork taint.

BACKGROUND ART

Mass spectrometry is an analytical technique which is widely used in many different fields of technology for the identification and quantification of individual substances or compounds of interest (so called analytes) in pure samples as well as in complex mixtures.

Mass spectrometry usually involves the measurement of the mass-to-charge ratio of ionized analytes or analyte ions, respectively. Thus, in a first step, analytes, which are typically neutral atoms or molecules, need to be ionized and transferred to a mass analyzer. Thereby, chemical ionization is particularly advantageous because this technique is selective and therefore can reach very low limits of detection, results in minimal fragmentation as well as a high degree of preservation of molecular identity and structure of the analytes.

In chemical ionisation, ionized analytes are produced through collisions of the analytes with reagent or primary ions which typically have been produced in a reagent ion source. In the reagent ion source, reagent ions can e.g. be created from a reagent gas (e.g. methane, ammonia, water, nitrogen oxide, oxygen and the like) by electron ionization, by plasmas, electromagnetic radiation (e.g. x-rays) or radioactive radiation.

However, the efficiency of providing ionized analytes by chemical ionization depends fundamentally on three aspects: (1) the generation of primary or reactant ions, (2) the reaction of the primary ions and analytes, and (3) the transfer of the analyte ions to a mass analyzer. In this regard, various experimental setups and instruments are known:

U.S. Pat. No. 5,175,431 (Georgia Tech Research Corporation) discloses a high pressure interface device for connecting a gas chromatograph to a mass spectrometer. In this system, a trace gas is ionized by radioactive radiation in a cryogenically cleaned buffer or carrier gas laminary flowing in a flow tube. As a source of radioactive radiation, radioactive material can e.g. be coated on a ring inside the flow tube or be placed on an injection needle for the analytes. Thereby analytes are introduced in axial direction in to the flow tube in a laminar flow region so that they will get ionized upon interaction with the ionized trace gas and transferred to the exit of the flow tube.

US 2014/0284204 A1 (Airmodus OY, University of Helsinki) describes a device for ionizing molecules and clusters by chemical ionization in a sample gas before entering an analyzer, such as a mass analyzer. Thereby, reagent gas is entered into an ion molecule reactor through an inlet which is arranged on one side of the chamber and ionized with a single x-ray source. Sample gas is introduced into the chamber via another inlet. This inlet is oriented along the longitudinal axis of the ion molecule reactor and perpendicular to the inlet of the reagent gas. Also in this setup, a laminar sheath gas flow is established between the sample gas and the wall structure of the device in order to guide the sample gas and the reagent ions. The trajectory of the reagent ions can be configured to bend from one side of the chamber inward and towards the sample gas flow at the interaction reaction. This can be achieved e.g. by using an electrical field, a deflector, a wing or a throttle, like a venturi tube for example.

However, these systems require high pressures, typically >100 mbar, of a buffer or sheath gas, respectively, in the flow chamber in order to establish laminar flow which is effective in guiding the reagent ions and analytes. This in turn requires highly pure gas to be used or special cleaning measures in order to avoid for example formation of undesired ionic species with impurities. Moreover, a high pressure in the ion molecule reactor will give rise to memory effects or long recovery times of the chamber, respectively. Also, additional measures are required in order to provide a buffer gas with a desired constant pressure or to establish a well-defined laminar flow.

A further concept is disclosed in US 2008/0217528 A1 (TOFWERK AG) which describes inter alia an ion molecule reactor in which reagent ions are produced in a high pressure reagent ion source and then fed in axial direction into an elongated chamber comprising cylindrical rod electrodes as an ion guide. Analyte molecules enter through a lateral sample inlet into the ion molecule reactor and are then ionized by reactions with reagent ions at the crossing point between the reagent ions and the analytes at the first end of the chamber.

However, with such a setup only limited analyte ion yields and limited sensitivity are achievable, in particular due to rather low interaction times between the reagent ions and the analytes.

Thus, in particular when it comes to screening applications of complex mixtures, it is difficult to satisfy industrial needs regarding sensitivity, selectivity and sample throughput with known techniques.

For example, in the wine industry, the screening of cork stoppers is desirable in order to reduce the change of later contamination of wine by contaminants present in the cork, resulting in "cork taint". "Cork taint" is a broad term describing wine which has undesirable smells or tastes, especially spoilage that can only be detected after bottling, aging and opening. However, screening of cork is a challenge due to extremely low concentrations of contaminants to be detected and the complex mixture of VOC (volatile organic compounds) emitted from cork and woody materials.

Halophenols or haloanisols are one class of such contaminants. Thereby, 2,4,6-trichloroanisole (TCA) is the most common contaminant which at higher levels, makes wine smell moldy or musty, like cardboard, damp cement or wet newspapers. In the worst case, the wine is undrinkable. TCA contamination is not hazardous to human health, however it poses a serious problem for wines closed with cork stoppers as it can effect wines irrespective of quality and price point.

TCA originates from chemical processing of the raw cork materials as cork is made into stoppers. TCA is formed, when special fungi are treated with chlorinated phenolic compounds, which are a type of antimicrobial agent used in the processing of wood. Very small amounts of this compound, on the order of nanograms/litre, can be responsible for this defect due to the extremely low concentrations of TCA (ng/L) which are perceptible by humans.

An efficient and preferably automated screening of corks for haloanisols such as TCA is therefore desirable to prevent damage during storage and fermentation of wine.

U.S. Pat. No. 9,588,089 B2 (Cevaque Invest) describes a method for analysing cork by gas chromatography (GC). However this approach is slow, if sufficient separation is to be achieved to reduce the number of false positives.

Thus, there is still a need to further improve techniques and instruments for chemical ionisation of analytes which are especially suitable for use in mass spectrometry. Moreover, there is a need to provide solutions for industrial screening applications involving complex mixtures.

SUMMARY OF THE INVENTION

It is the object of the present invention to provide improved devices and methods pertaining to the technical field initially mentioned. Especially, improved devices and methods for detecting and analysing analytes with a high sensitivity and allowing for a high sample throughput shall be provided. Especially, the devices and methods shall be suitable for detecting cork taint and/or haloanisols with higher sensitivity, and, especially with sufficient specificity or separation to reduce false positive rates. In particular, improved techniques and instruments for chemical ionisation of analytes shall be provided which are especially suitable for use in mass spectrometry. Thereby, it is desirable to achieve as high analyte ion yields as possible. Also devices and methods should be provided which can improve the sensitivity in mass spectrometry and/or which allow for measuring analytes in ultra-low concentrations, e.g. concentrations in the range of a few ppqv (parts per quadrillion by volume) such as in atmospheric sciences or in wine industry among others. Moreover, the techniques and instruments should be as fail-safe and as easy to use as possible.

The solution according to this invention is inter alia specified by the features of claim 1. Thus, according to the invention an ion molecule reactor for generating analyte ions from analytes, in particular for use with a mass analyzer and/or in mass spectrometry, comprises:

- a) a reaction volume in which reagent ions can interact with the analytes in order to form analyte ions, especially by chemical ionisation;
- b) at least one analyte inlet which allows for introducing the analytes along an inlet path into the reaction volume, whereby, preferably, a direction of the inlet path runs essentially along a direction of at least a first section of the predefined transit path in the reaction volume;
- c) at least one reagent ion source and/or at least one reagent ion inlet which allows for providing reagent ions into the reaction volume;
- d) optionally, at least one ion guide comprising an electrode arrangement which is configured for producing an alternating electrical, magnetic and/or electromagnetic field, that allows for guiding the reagent ions and/or the analyte ions at least along a section of the predefined transit path, especially along a first section of the transit path, preferably along the whole transit path, through the reaction volume.

In the present context, the term "ion guide" stands for a device for changing a velocity of ions with an alternating electrical, magnetic and/or electromagnetic field. Preferably, a frequency of the alternating electrical, magnetic and/or electromagnetic field is about 0.01-100 MHz, particularly 0.1-10 MHz, especially 0.5-5 MHz.

However, if desired, one or more DC field can be applied in addition to the alternating electrical, magnetic and/or electromagnetic field.

The ion guide, if present, is configured to selectively change the velocity of ions, especially without affecting a velocity of neutrals. Thereby the term "velocity" is to be understood as a vector with a direction and magnitude. Thus, when changing the velocity, the direction and/or magnitude of the respective ion are changed. Especially, with the ion guide ions can be accelerated and/or decelerated and/or the direction of movement can be changed. Thereby, the ion guide allows for guiding and/or focussing the analyte ions and/or the reagent ions along the transit path within the reaction volume. In particular, the ion guide provides an ion channel for the analyte ions. Thereby, in particular, the ion channel essentially corresponds to the transit path.

The "reaction volume" is a volume in space within the ion molecule reactor in which ionization of the analytes by collisions with reagent ions takes place. Especially, the reaction volume is the volume in which the ion guide is effective or in which ions are effectively guided, respectively. In particular, the reaction volume is at least partially enclosed in housing and/or a tubular element. In particular, the housing is a tubular element.

The term "predefined transit path" stands for the path on which the analyte ions are guided through the reaction volume and/or for the path along which the analyte ions are intended to move along. The transit path can e.g. be a curved line, a straight line or a line with one or more straight and/or one or more curved sections. Preferably, with respect to the intended direction of movement of the analytes, at least a first section of the predefined transit path runs along a straight line. Especially, a length of the first section, preferably a straight line, is at least 5%, preferably at least 10%, in particular at least 25%, advantageously at least 50%, particularly preferred at least 75%, of the length of the whole transit path through the reaction volume. In particular, the transit path runs along a central and/or longitudinal axis of the reaction volume and/or of the ion molecule reactor.

The "analyte inlet" comprises in particular a hollow tubular inlet, especially a cylindrical tube. Thereby, the analytes can be guided through the tubular inlet into the ion molecule reactor and/or the reaction volume. Preferably, the analyte inlet and/or the analyte inlet path runs in parallel or coaxially with a longitudinal axis of the ion guide and/or the ion molecule reactor.

The "inlet path" is the path along which the analytes are introduced into the reaction volume and/or the ion molecule reactor. In particular the inlet path is an essentially straight line. Preferably, the inlet path runs essentially perpendicular to an inlet opening or an inlet orifice of the analyte inlet and/or the inlet path runs along a longitudinal axis of a tubular end of the analyte inlet. Thereby, the tubular end of the analyte inlet ends in the ion molecule reactor.

Surprisingly, it was found that the inventive setup allows for specifically direct and focus reagent ions within the reaction volume and achieve a high density of reagent ions in an extended section of the reaction volume where the reagent ions can interact with the analytes. Hence, the spatial distribution of the reagent ions can be controlled very efficiently with the inventive setup. Additionally, analyte ions can be guided through the reaction volume along the predefined transit path.

Moreover, the inventive introduction of the analytes into the reaction volume along a direction of at least a first section of the predefined transit path through the reaction volume furthermore results in a high density of analytes in the reaction volume. At the same time, the density of unnecessary and lost analytes outside the reaction volume can be kept low. Thus, with the inventive setup relatively high densities of reagent ions as well as analytes are obtainable in the reaction volume. This in turn allows for a very efficient chemical ionisation of the analytes, because the probability of collisions with reagent ions is increased.

This is e.g. in strong contrast to a setup where analytes are introduced into an ion molecule reactor in a direction essentially perpendicular to the predefined transit path, such as e.g. according to US 2008/0217528 A1, where essentially all of the analytes which are not ionized immediately at the crossing point with the reagent ions are lost. Hence, in such a setup only a very limited volume of interaction between the reagent ions and the analytes is available.

With the inventive setup it is for example possible to detect specific analytes in a highly complex mixture comprising the analytes in a concentration of 100 ppt or less, especially 1 ppt or less, in particular 0.1 ppt or less, for example 0.01 ppt or less, particularly 0.001 ppt or less. Therefore, the inventive setup can be used to directly analyse complex samples, such as e.g. volatile organic compounds evaporated from cork stoppers, without the need for further separation or concentration of the analytes of interest.

Moreover, because of the inventive setup, reagent ions can be kept for a longer time within the reaction volume what further enhances the probability of collisions with analytes or the ionization efficiency of analytes, respectively. Also, analyte ions produced by collisions with reagent ions can be guided by the ion guide through the reaction volume on the predefined path. Hence, loss of reagent ions or analyte ions by collision with other atoms or molecules present in the ion molecule reactor or with elements of the ion molecule reactor, such as walls and the like, can greatly be reduced.

As it turned out, the functional and synergistic interplay between the special way of introducing the analytes into the reaction volume and the specific ion guide, if present, greatly increases the efficiency of chemical ionisation and allows for providing ionized analytes with a surprisingly high yield.

Thereby, the ion molecule reactor can be operated at pressures well below 10 mbar. Thus the problem of undesired impurities and loss of analyte ions by a high rate of collisions with non-analyte gas associated with systems using high pressure buffer or sheath gas can be greatly reduced.

Moreover, with the inventive setup, analyte ions as well as primary ions can effectively be guided along spatially well-defined paths within the reaction chamber. This allows for keeping the ions away from the walls of the ion molecule reactor which results in a low rate of adsorption of the ions on the walls of the ion molecule reactor. Consequently, the number of ions or molecules later on desorbing from the ion molecule reactor walls will be on a low level as well. Overall this results in a reduced memory effect.

A reduced memory effect in turn leads to reduced recovery times of the ion molecule reactor so that the reactor can be reused more quickly after a measurement. Also, if the ion molecule reactor is for example used for time resolved measurements of varying analyte concentrations, the time resolution of the measurements can be greatly improved. Accordingly, if varying concentrations of analytes are to be measured, a low number of unwanted and previously adsorbed analyte ions or molecules desorbing from the ion molecule reactor walls back into the reaction volume or the transit path will ensure a minimal effect on the actual analyte concentration. Therefore, fluctuations in analyte concentrations can be measured with higher precision or with higher time resolution, respectively.

If the walls of the ion molecule reactor furthermore comprise at least one porous and/or gas permeable section, ions as well as neutrals reaching the walls of the ion molecule reactor additionally can at least partly be removed from the walls, e.g. by pumping. This will furthermore reduce the number of unwanted ions or molecules desorbing from the ion molecule reactor walls back into the reaction volume and thus reduce the memory effect. More details with regard to embodiments comprising porous and/or gas permeable sections in the walls of the ion molecule reactor are given below.

In particular, the sensitivity in mass spectrometry can be increased by at least one order of magnitude with the inventive ion molecule reactor, especially in proton transfer reaction based chemical ionization systems.

Preferably, the reagent ion source and/or the reagent ion inlet is located radially outwards with respect to the first section of the predefined transit path and/or the inlet path. This allows for a highly compact setup as well as an efficient introduction of reagent ions into the reaction volume. However, other arrangements may be suitable as well.

Especially, the at least one reagent ion source and/or the at least one reagent ion inlet preferably is configured such that the reagent ions can be introduced into the reaction volume along at least two distinct directions and/or from at least two distinct positions. The at least two distinct directions are in particular non-parallel directions, preferably both intersecting the inlet path and/or the first section of the transit path. The at least two distinct positions are two positions separated in space. Preferably, the at least two distinct positions are located in at least two different radial directions with respect to the inlet path and/or the analyte inlet. Thereby, the at least two different radial directions run essentially perpendicular to the direction of the inlet path and/or the analyte inlet. Especially, the at least two distinct positions are comprised within an area of an annulus sector or an annular area surrounding the inlet path and/or the analyte inlet. Especially, an angle between the two radial directions, where the two most distant of the at least two distinct positions are located, is at least 2°, for example at least 5°, especially at least 10°, in particular at least 22.5°, for example at least 30°, advantageously at least 45°, particularly at least 45°, especially preferred at least 60°, for example at least 90°, at least 120°, or at least 180°. In between the two most distant positions, any number of additional positions may be present.

If there are several reagent ion sources and/or analyte inlets, preferably all of the reagent ion sources and inlets are configured such that the reagent ions can be introduced into the reaction volume along at least two distinct directions and/or from at least two distinct positions.

Surprisingly, it was found that such a setup allows for even more efficiently providing and introducing reagent ions into the reaction volume. When the reagent ions are introduced into the reaction volume along at least two distinct directions and/or from at least two distinct positions, it is possible to specifically direct and focus the reagent ions towards the reaction volume and further increase the density of reagent ions in an extended section of the reaction volume. Hence, the spatial distribution of the reagent ions can be very precisely controlled with such a setup. Specifically, this setup will further reduce the tendency of reagent ions to diverge and collide with the wall when entering the reaction volume.

Nevertheless, for example for special applications, other arrangements may be beneficial as well.

The ion molecule reactor can comprise at least one reagent ion source which can be installed within the ion molecule reactor and/or outside the ion molecule reactor. Also, it is possible to have different reagent ion sources inside and/or outside the ion molecule reactor at the same time. Instead or additionally to the at least one reagent ion source, the ion molecule reactor may comprise at least one reagent ion inlet. In this case, reagent ions can e.g. be produced with an external reagent ion source and then be guided through the reagent ion inlet into the ion molecule reactor. The reagent ion inlet may for example be a tubular inlet, optionally with elements for guiding the reagent ions. Preferably, the ions source is configured to produce an overall beam of reagent ions which is directed and/or focussed towards the reaction volume.

Especially, the at least one reagent ion source and/or the at least one reagent ion inlet is configured to produce one or more beams of reagent ions with an inlet direction which runs at an angle of 0-100°, in particular 5-100°, especially, 45-95°, for example 60-90° or essentially orthogonal, to the direction of the inlet path and/or the first section of the transit path. However, especially in connection with beams of reagent ions which are ring-sector shaped, ring-shaped, disc-shaped, in particular as described below, the one or more beams of reagent ions preferably run at an angle of 0-10°, more preferably 0-5°, most preferably 0° to the direction of the inlet path and/or the first section of the transit path.

With such a setup, the reagent ions can be directed and/or focussed directly into the reaction volume or the first section of the transit path. This will give rise to a high concentration of reagent ions in the reaction volume.

Nevertheless, reagent ion sources and/or ion inlets with other characteristics may be used as well.

Preferably, the at least one reagent ion source and/or the at least one reagent ion inlet is configured to produce an overall beam of reagent ions with rotational symmetry or circular symmetry. Put differently, the overall beam of reagent ions is axis-symmetric in this case. Thereby the symmetry is preferably given with regard to an axis defined by the direction of first section of the transit path, the analyte inlet and/or the inlet path. The rotational symmetry can e.g. be an n-fold symmetry with $n \geq 2$. Circular symmetry is given if $n \to \infty$. The "overall beam" is meant to be the sum or superposition of all partial beams originating from the at least one reagent ion source and/or the at least one reagent ion inlets or from all of the reagent ion sources and all of the reagent gas inlets together. Thereby, the reagent ions are introduced into the reaction volume along at least two distinct directions and/or from at least two distinct positions.

Such kind of symmetric reagent ion beams have been shown to be highly beneficial for achieving a high density of reagent ions with essentially homogeneous distribution in the reaction volume.

However, for example for special applications, reagent ion sources with an overall beam without rotational or circular symmetry can be used as well.

In particular, the reagent ion source is configured to produce an overall ring-sector shaped, ring-shaped, disc-shaped and/or cone-shaped beam of reagent ions, especially a ring-shaped beam of reagent ions. Thereby, preferably, the beam is axis symmetric with regard to an axis defined by the direction of first section of the transit path, the analyte inlet and/or the inlet path. In particular, a cone-shaped beam can have a form of a conical surface or of a conical volume.

In a ring-shaped or disc-shaped beam, the reagent ions move in particular from an outer circumference towards a central longitudinal axis of the ring-shape or the disc-shape, respectively.

With a cone-shaped beam, the reagent ions move in particular from a base towards the apex of the cone. Also, if present, a cone-shaped beam is preferably oriented such that an apex of the cone-shaped beam is directed towards the reaction volume, in particular onto the first section of the transit path.

In any case, with such ion beams the reagent ions can in principle be introduced into the reaction volume along an infinite number of distinct directions and/or from an infinite number of distinct positions. This allows for further increasing the density and homogeneity of the reagent ions in the reaction volume. This in turn will increase the efficiency of ionisation reactions in the reaction volume and improve the yield of analyte ions.

Especially preferred, the at least one reagent ion source and/or the at least one reagent ion inlet is of annular shape and/or has a shape of one or more ring sectors. Preferably the at least one reagent ion source and/or the at least one reagent ion inlet is/are arranged coaxially around the first section of the transit path, the inlet path and/or the analyte inlet. Especially preferred, the ion molecule reactor comprises exactly one annular reagent ion source or exactly one annular reagent ion inlet.

With such a setup, it is in particular possible to produce axis symmetrical beams of reagent ions with highly homogeneous distribution. Also, with a reagent ion source and/or a reagent ion inlet of annular shape and/or which has a shape of one or more ring sectors, the reagent ions can be introduced into the reaction volume along at least two distinct directions and/or from at least two distinct positions in an easy and reliable manner.

According to another advantageous embodiment, the ion molecule reactor comprises at least two, especially at least three, four, five, six, seven or even more, individual reagent ion sources and/or reagent ion inlets, which are preferably arranged on a circular line around the first section of the transit path, the inlet path and/or the analyte inlet, whereby, preferably, the circular line is concentric with regard to the first section of the transit path, the inlet path and/or the analyte inlet.

Especially, if present, the at least two individual reagent ion sources and/or the at least two individual reagent ion inlets are arranged symmetrically around the first section of the transit path, the inlet path and/or the analyte inlet.

With at least two individual reagent ion sources and/or reagent ion inlets, the partial beams of reagent ions from the two sources and/or inlets can be controlled flexibly and thus be introduced into the reaction volume independently along the at least two distinct directions and/or from the at least two distinct positions. However, it is still possible to obtain a high density and homogeneous distribution of reagent ions in the reaction volume. This is in particular true with a symmetrical arrangement.

In particular, the at least one reagent ion source and/or the at least one reagent ion inlet comprises a ring-shaped nozzle and/or a ring sector-shaped nozzle. In particular, these nozzles have at least one ring-shaped and/or slit-shaped opening. Also it is possible that several openings, e.g. round and/or elongated openings, are arranged in a ring-like manner.

Such kind of nozzles allow as well for producing axis-symmetrical beams of reagent ions with highly homogeneous in a reliable manner.

Nevertheless, it is for example possible to use other nozzles instead of or additionally to ring-shaped and/or ring sector-shaped nozzles. For example, the at least one reagent ion source and/or the at least one reagent ion inlet can have two individual tubular nozzles.

According to a further preferred embodiment, the at least one reagent ion source and/or the at least one reagent ion inlet comprises at least one guiding element for guiding reagent ions before entering the reaction volume. Thus, the guiding element is different from the ion guide for guiding the reagent ions and/or the analyte ions at least along a section of the predefined transit path through the reaction volume. Specifically, in a direction of movement of the reagent ions, the guiding element is located in front of the reaction volume.

Preferably, the guiding element is configured to produce an electrical, magnetic and/or electromagnetic field that allows for guiding the reagent ions before entering the reaction volume, in particular by focusing, accelerating and/or decelerating the reagent ions. By doing so, the reagent ions can be directed flexibly and with high precision into the reaction volume with a predefined energy and/or velocity. This further increases the ionization rate of analytes in the reaction volume what in turn will increase to overall yield of analyte ions produced in the ion molecule reactor. Also, if a change from one reagent gas to another reagent gas is made, the guiding element of the at least one reagent ion source and/or the at least one reagent ion inlet allows for compensating different characteristics of the reagent gases in a quite easy and efficient manner without need for changes in the mechanical setup.

Especially, if present, the guiding element of the at least one reagent ion source and/or the at least one reagent ion inlet comprises an electrode arrangement, preferably comprising at least two electrodes. For example the guiding element comprises a multipole electrode arrangement, an ion funnel and/or an ion carpet. The electrode arrangement, multipole electrode arrangement, the ion funnel and/or the ion carpet of the guiding element can be similar to the multipole electrode arrangement, the ion funnel and/or the ion carpet as described in connection with the ion guide below.

However, guiding elements of the at least one reagent ion source and/or the at least one reagent ion inlet are only optional and can be omitted.

If present, the at least one reagent ion source is preferably selected from electrical discharge based reagent ion sources, plasma based reagent ion sources, photoionization based reagent ion sources, x-ray reagent ion sources and/or radioactive reagent ion sources. For example, the reagent ion source is a glow discharge based reagent ion source, a radio frequency based reagent ion source, a microwave based reagent ion source, a corona discharge based reagent ion source and/or a dielectric barrier glow discharge based reagent ion source.

Such kinds of reagent ion sources are in principle known to the person skilled in the art and allow for a well controllable ionisation of a reagent gas to form specific reagent ions. Nevertheless, for specific applications, it might be beneficial to use other reagent ion sources.

Preferably, the reagent ions used in the present invention are positively charged ions, such as e.g. $H_3O^+$, $O_2^+$, $CH_4^+$, $NH_4^+$, isobutane ions, and/or $NO^+$. Thus, the ions source is in particular capable of producing these types of ions. However, other reagent ions, including negatively charges ions, might be suitable as well.

Especially preferred, $H_3O^+$ is as the reagent ions in the present invention. This allows for generating analyte ions by Proton-Transfer-Reaction (PTR), a process which is highly beneficial in connection with analysing volatile organic compounds (VOC).

However, for analysing haloanisols, such as e.g. TCA, it turned out that positively charged reagent ions, such as e.g. $O_2^+$ and/or $NO^+$, especially $NO^+$, are particularly preferred.

The ion guide comprises in particular an electrode arrangement with at least two, in particular at least three, especially at least four, preferably at least five, particularly at least six or at least eight electrodes, for generating an alternating electrical, magnetic and/or electromagnetic field for guiding, focusing, accelerating and/or decelerating ions, in particular analyte ions and reagent ions, within the reaction volume and/or along the predefined transit path. Especially, the ion guide can comprise an electrode arrangement with exactly two, three, four, five, six or eight electrodes. The electrodes are in particular selected from conductive rods, ring electrodes, coatings and/or stripes.

Especially, the electrode arrangement is configured for generating a guiding field for guiding and/or focussing ions, in particular analyte ions and/or reagent ions, along the transit path. This guiding field preferably is an electromagnetic field, especially a radiofrequency (RF) field, generating an effective potential confining the ions to a region along the transit path. Such a guiding field greatly helps to focus the ions in the reaction volume and preventing them from hitting the walls of the ion molecule reactor. This in turn will greatly increase the overall yield of analyte ions.

Preferably, the electrode arrangement is configured for generating a transport field for accelerating and/or decelerating ions in a direction along the transit path. With such a transport field, for example, the reaction time between reagent ions and analytes can be controlled very precisely. Especially, this transport field is an electrical field, especially a DC field, which runs essentially along the transit path. However, the first field may as well be a superposition of electromagnetic fields.

In particular, the electrode arrangement is configured for generating a rotating field. Preferably, the rotating field results in an ion motion orbiting around the mean flight path of the ions. This allows in particular for setting a constant energy of the ions. A possible implementation of such an electrode arrangement in a multipole arrangement is described below. However, other implementations might be suitable as well.

Most preferred, the ion guide comprises an electrode arrangement which is configured for generating a transport field independently of the guiding field. Even more preferred, the ion guide comprises an electrode arrangement which is additionally configured for generating a rotating field. With such a setup, the velocity of the ions along the predefined path can be controlled independently of the focussing and/or guiding of the ions in a highly efficient manner.

However, other means for guiding neutrals and/or ions may be used alternatively or additionally as well.

In particular, the ion molecule reactor comprises at least one voltage generator which can be electrically connected to the ion guide or the electrode arrangement of the ion guide or the at least two electrodes, respectively. Especially, the at least one voltage generator is capable of providing alternating voltage and optionally direct voltage in addition. Preferably, there are at least two voltage generators or at least one voltage generator with at least two individually controllable outputs, whereby a first voltage generator or a first output, respectively, can be connected to a first electrode and a second voltage generator or a second output, respectively, can be connected to a second electrode. Thereby, each of the electrodes can be used for separately generating electrical and/or electromagnetic fields.

In particular, if a guiding element of the at least reagent ion source and/or the at least one ion inlet is present, the ion molecule reactor comprises at least one further voltage generator which can be electrically connected to the guiding element.

Preferably, the ion guide comprises a multipole electrode arrangement, an ion funnel and/or an ion carpet.

An ion funnel can for example comprise a stack of at least two electrodes, especially ring electrodes whose inner diameter gradually decreases. Preferably, an ion funnel comprises at least three, four, five or even more electrodes. In particular, the ring electrodes are arranged coaxial with regard to the analyte inlet and/or at least a first section of the predefined transit path in the reaction volume or that a longitudinal axis of the ion funnel is arranged coaxially with respect to the analyte inlet and/or at least a first section of the predefined transit path in the reaction volume.

The ion funnel is preferably configured such that in operation reagent ions and/or analyte ions are radially confined as they pass through the ion funnel. Especially, in operation, out-of-phase alternating potentials, e.g. radio frequency potentials, can be applied to adjacent electrodes. Put differently, the phase of the voltage, alternates from electrode to electrode. Additionally, a direct voltage gradient (DC gradient) can be applied in the direction of the longitudinal axis of the ion funnel in order to accelerate and/or decelerate the ions.

An ion carpet preferably comprises an essentially planar arrangement of at least two electrodes, preferably a plurality of electrodes, e.g. dots, strips and/or rings, that can each have different voltages applied to them. The electrodes themselves can be arranged in a radial pattern and/or in linear arrays. According to a highly advantageous embodiment, the electrodes comprise at least two or more individual concentric rings.

Especially, the electrodes are surrounding an orifice in the ion carpet. Thereby, in operation, voltage is applied to the electrodes of the ion carpet, such that an alternating electric field is generated which funnels reagent ions and/or analyte ions through the orifice. Sometimes, ion carpets are also called planar ion funnels. A highly beneficial embodiment of a planar ion funnel and its operation is described in US 2013/0120897 A1 (Amerom et al.).

Especially preferred, the ion guide comprises a multipole electrode arrangement, for example a quadrupole and/or an octapole electrode arrangement. The multipole electrode arrangement preferably comprises elongated electrodes being arranged along and/or around the transit path. In this case, preferably, the transit path runs along a longitudinal multipole axis, e.g. along a quadrupole axis.

Such an arrangement is especially preferred for generating a guiding field for guiding and/or focussing ions along the transit path. It is known that an oscillatory inhomogeneous electrical field forms a so-called effective potential which is proportional to $E^2$, where E is the amplitude of the electrical field strength oscillations (see e.g. Landau L. D., Lifshitz E. M.: Mechanics, Pergamon Press, Oxford 1976: Gerlich, D. "Inhomogeneous Electrical Radio Frequency Fields: A Versatile Tool for the Study of Processes with Slow Ions" in: State-Selected and State-to-State Ion-Molecule Reaction Dynamics, edited by C. Y. Ng and M. Baer. Advances in Chemical Physics Series, LXXXIL 1, 1992). In case of a quadrupolar RF electrical field the effective potential results in a net force on the ion towards the quadrupole axis. This force is inverse proportional to the ion mass-to-charge ratio (m/Q) and directly proportional to the ion distance from the quadrupole axis. This fundamental property of the effective potential results in that an ion with a given m/Q will perform slow oscillations around the quadrupole axis with a characteristic frequency which is inversely proportional to its m/Q. i.e. the quadrupole field and similarly higher multipole fields are confining fields suitable for guiding and focussing analyte ions and/or reagent ions according to the present invention.

Linear RF multipole fields that are particularly well adapted for the inventive ion guide are usually produced using co-axial rods of parabolic or circular shape. Other shapes may be used e.g. in order to approximate quadrupole fields. Preferably, a primary RF-only field is applied between opposing set of electrodes or rods.

In a particularly preferred embodiment a rotating multipole field is generated at the at least one electrode, in particular a rotating quadrupole field. In principle, the utilization of such fields is known, e.g. from fundamental kinetic studies (see V. V. Raznikov, I. V. Soulimenkov, V. I. Kozlowski, A. R. Pikhtelev, M. O. Raznikova, Th. Horvath, A. A. Kholomeev, Z. Zhou, H. Wollnik, A. F. Dodonov: "Ion rotating motion in a gas-filled radio-frequency quadrupole ion guide as a new technique for structural and kinetic investigations of ions"; Rapid Communications in Mass Spectrometry; Volume 15, Issue 20, Pages 1912-1921). When properly tuned, such a rotating field can result in an ion motion orbiting around the mean flight path of the ions. This makes it possible to set the ion or energy, respectively, independently of the focussing and/or transport field. Also, the length of the flight path can be increased thanks to the rotating field which in turn increases the probability of ionization of analyte molecules.

Further details of suitable arrangements of electrodes and operations thereof are given in US patent application US 2008/0217528 A1 (Tofwerk AG).

According to a special embodiment, the ion guide comprises at least two different multipole electrode sections. For example the ion guide comprises a quadrupole section which is followed by an octupole section. Thereby, a first section, for example the octupole section, can e.g. be adapted or used for compressing reagent ions in order to increase ionisation reactions with analytes, whereas the second section, e.g. the quadrupole section, is used for focusing and/or guiding analyte ions along the transit path. Such an arrangement will further enhance the overall efficiency of the process However, multipole arrangements are optional and can be omitted if not required. Also more complex multipole arrangements can be foreseen for special applications.

Instead or in addition of a multipole, for example an ion funnel and/or an ion carpet as described above can be used. Also, any other ion guide comprising an electrode arrangement which is configured for producing an alternating electrical, magnetic and/or electromagnetic field, that allows for guiding the reagent ions and/or the analyte ions at least along a section of the predefined transit path, preferably along the whole transit path may be suitable.

According to a special embodiment, the ion guide comprises a multipole arrangement, especially as described above, in combination with an ion funnel and/or an ion carpet, preferably as described above. It was found that such a setup even better allows for specifically directing and focussing reagent ions within the reaction volume and achieving a high density of reagent ions in an extended section of the reaction volume. Hence, the overall yield of analyte ions can further be improved.

Especially, the ion funnel and/or the ion carpet is arranged in a direction of the transit path behind the ion guide. This allows for specifically extracting analyte ions in a defined direction and with a high yield out of the reaction volume.

However, such combinations of different ion guiding elements are optional and can be omitted if not desired or required, respectively.

Preferably, the ion molecule reactor further comprises a tubular element at least partially, preferably fully, surrounding the reaction volume and/or the transit path. The tubular element is preferably of cylindrical shape, especially with a circular cross section. However, rectangular or square cross-sections are possible as well. Moreover it is possible to use tubular elements with at least two different cross-sections. Also, the tubular element can be straight or bent.

Especially a length of the tubular element in a longitudinal direction is >10 mm, especially >100 mm, in particular >500 mm, particularly >1,000 mm, >2,000 m, >5,000 mm or >10,000 mm. An inner diameter to length-ratio of the tubular element may for example be between 1:1.5-1:5,000, particularly 1.1-500, especially 1:2-1:50, in particular 1:5-1:20. A ratio of the wall thickness if the tubular element to the inner diameter may for example be between 1:1-1:50, especially 1:5-1:20.

The tubular element can at least partially or fully be flexible or bendable, e.g. when made from plastics material. However, it is also possible to use a rigid tubular element, for example made out of glass and/or ceramics. An embodiment with a bendable tube makes it for example possible to use the ion molecule reactor as a probe or a probe head, respectively, e.g. for taking analyte samples at random positions. Thereby, ions might be transferred over quite long distances, e.g. over several meters. This might work similar to a vacuum cleaner.

If the ion molecule reactor comprises at least one electrode as described above, the at least one electrode can be arranged inside the tubular element, within the walls of the tubular element and/or outside the tubular element. Also, it is possible to apply a coating onto the tubular element which can serve as an electrode. In a preferred embodiment, at least one electrode is made from a material with lower electrical resistivity than the material of the tubular element.

Especially preferred, at least one electrode is arranged within the walls of the tubular element and/or outside the tubular element. This helps in particular to reduce contamination of the electrodes.

If the at least one electrode is of elongated structure, at least one electrode can be positioned in a longitudinal direction with respect to the tubular element and/or wound around the tubular element. However, other arrangements are possible as well.

In a particular embodiment, the tubular material is made of an electrically isolating material and/or of a material of high ohmic resistance, for example of perfluoralkoxy polymers (PFA), e.g. Teflon, and/or of polytetrafluorethylen (PTFE). In this case, the tubular element can be used as the at least one electrode or as a further electrode, in particular as an electrode for generating a transport field, especially an electrical field, e.g. a DC field. However it is also possible to use ring electrodes instead or in addition to the electrode in the form of the tubular element.

Further details about tubular elements and possible arrangements of electrodes are given in US patent application US 2008/0217528 A1 (Tofwerk AG).

Especially, the tubular element comprises at least one porous and/or gas permeable section in particular for introducing a fluid into the reaction volume and/or for removing neutrals and ions having left the predefined transit path out of the reaction volume and/or the ion molecule reactor. In a special embodiment, the tubular element is porous and/or gas permeable along its whole length. Especially, the porous and/or gas permeable section covers at least 5%, in particular at least 25%, especially at least 50% or at least 75% of the surface of the tubular element.

The at least one porous and/or gas permeable section can e.g. comprise a filter, a mesh and/or a frit. Especially, the at least one porous or gas permeable section surrounds the reaction volume at least along a partial section of the transit path or along the full transit path in the reaction volume. Preferably, the at least one porous or gas permeable section is a ring-shaped or annular section of the tubular element.

The fluid can e.g. be a sheet and/or buffer gas which can be introduced in the ion molecule reactor, especially in a radial direction, e.g. in order to reduce wall or memory effects. The fluid can be introduced into the ion molecule reactor for example driven by a pressure difference between inside and outside pressure of the tubular element.

However, it is also possible to introduce a reagent gas and/or reagent ions through the at least one porous and/or gas permeable section of the tubular element, especially in a radial direction, into the reaction volume. In this case, the at least one porous section of the tubular element has the function of a reagent ion inlet. The reagent ions can for example be produced outside the tubular element with a reagent ion source as described above.

When removing neutrals and ions having left the predefined transit path out of the reaction volume and/or the ion molecule reactor through the porous and/or gas permeable section, the efficiency of the ion molecule reactor can further be improved since wall and memory effects can be reduced and the overall pressure in the reaction volume can be reduced. Thus at the same exit pressure, higher analyte ion yields are achievable.

Advantageously, in a longitudinal direction, the tubular element has at least one first section which is non-porous or gas-tight and a second section which is porous or gas permeable. Preferably, the gas tight section is oriented towards the analyte inlet whereas the gas permeable section is oriented downstream with regard to the direction of movement of the analyte ions. With such a setup, the ionisation reaction of the analytes with the reagent ions can take place in the gas-tight sections which is beneficial in terms of ionisation yield of analyte ions. Further downstream, the efficiency of analyte ion transfer can be increased due to the porous or gas permeable section which allows for reducing the density of non-ionized analytes and other substances.

According to a further preferred embodiment, the tubular element is comprised within an outer tubular element. In particular, the outer tubular element is gas-tight or non-porous. For example it is made of stainless steel.

Especially, the inner diameter of the outer tubular element is larger than the out diameter of the tubular element. Thus, in this case, there is a free volume between the tubular element and the outer tubular element. This volume can e.g. be used to provide a fluid, e.g. a gas, which is to be introduced trough a porous section or gas permeable section of the tubular element in to the reaction volume. Also it is possible to reduce the pressure within the free volume to a value below a pressure in the reaction volume in order to remove neutral analytes and other substances from the reaction volume driven by a pressure difference.

Preferably, the outer tubular element comprises an opening for introducing fluids and/or for evacuating the free volume between the two tubular elements.

Preferably, the ion molecule reactor comprises a housing, in particular an elongated housing, especially a cuboidal and/or cylindrical tubular member, with a longitudinal axis. Preferably the housing has an exit orifice for the analyte ions. If there is a tubular element and/or an outer tubular element, it can be part of the housing. Especially, the analyte inlet and/or the analyte inlet direction runs in parallel or coaxially with a longitudinal axis of the housing and/or the analyte inlet direction is directed towards the exit orifice.

If the analyte inlet direction is directed towards the exit orifice, the analytes and analyte ions can for example move along an essentially straight line through the reaction volume. Thus it is possible to define a straight transit path which can be beneficial in terms of efficiency and analyte ion yield.

Especially, the ion molecule reactor comprises a housing with an exit orifice for the analyte ions whereby, preferably, an aperture area of the exit orifice is from 0.002-79 mm$^2$, especially 0.03-20 mm$^2$, in particular 0.07-7 mm$^2$, preferably 0.2-3.1 mm$^2$, 0.4-1.8 mm$^2$. Especially, the exit orifice is circular with an aperture diameter of the exit orifice from 0.05-10 mm, especially 0.2-5 mm, in particular 0.3-3 mm, preferably 0.5-2 mm or 0.7-1.5 mm.

Thus, compared with ion molecule reactors known so far, the aperture area or aperture diameter, respectively, of the exit orifice can be reduced without significant losses of analyte ions. This is due to the inventive setup which allows for effectively focussing and guiding reagent ions and/or analyte ions within a well-defined and radially narrow area. Therefore, even exit orifices with rather small aperture areas or aperture diameters can be used.

Since the conductance (volume flow rate: e.g. in liter per seconds) of the exit orifice is proportional to the aperture area, the smaller the aperture area of the exit orifice, the lower the conductance of the exit orifice. Thus, with a small aperture area exit orifice, less unwanted gas exits the ion molecule reactor into subsequent chambers through the exit orifice. This in turn allows to keep a predefined pressure in subsequent chambers with smaller pumps or with pumps with lower pumping capacities, respectively. With smaller pumps it is possible to realize more compact instruments using ion molecule reactors.

For example, in the case of a circular exit orifice, the aperture area is proportional to the square of the aperture diameter. A reduction of the aperture diameter by a factor of 10 therefore will reduce the aperture area by a factor of 100. Thus, the aperture diameter is a highly effective parameter for controlling the conductance of the exit orifice and the overall size of the instrument using the ion molecule reactor.

Preferably, the ion molecule chamber is operated under such conditions that a cross sectional area of the beam of analyte ions reaching the exit orifice is equal or smaller than an aperture area of the exit orifice. Under such conditions, the yield of analyte ions is maximum.

The ion molecule reactor can be used for mass spectrometry. Thus, the present invention is furthermore concerned with a mass spectrometer comprising an ion molecule reactor according as described above.

The mass spectrometer can for example comprise a time-of-flight mass analyzer, a quadrupole mass analyzer, an ion trap analyzer, a sector field mass analyzer, a Fourier transform ion cyclotron resonance analyzer, an Orbitrap analyzer, especially in an analyzer housing. However, it is possible to make use of other mass analyzers as well.

Thereby, the ion molecule reactor is in particular connected to the mass analyzer such that analyte ions produced in the ion molecule reactor can be introduced into the mass analyzer. If required, a transfer device, e.g. an ion transfer tube, can be arranged between the ion molecule reactor and the mass analyzer. This allows for example for providing one or more intermediate pressure regions between the ion molecule reactor and the mass analyzer. Since mass analyzers are typically operated under high vacuum conditions, the pressure can be reduced stepwise with such measures.

Also, it is possible to foresee additional mass and/or energy filters between the ion molecule reactor and the mass analyzer.

Advantageously, the ion molecule reactor comprises a housing as described above. With such a setup, the ion molecule reactor can easily be attached to various mass analyzers which are comprised in an analyzer housing. However, in principle, it is also possible to include the ion molecule reactor and the mass analyzer in a common housing.

Also, the present invention is related to a kit of parts or an arrangement comprising an ion molecule reactor or a mass spectrometer as described above as well as a sampler for collecting at least one analyte from a sample, in particular from a solid sample.

However, it should be noted that the sampler for collecting at least one analyte from a sample can be of use independently of the other components of the ion molecule reactor, the kit of parts, the arrangements or the setups described herein. For example, the sampler for collecting at least one analyte from a sample can be used in connection with chromatography or extraction.

Especially, the sampler is a headspace sampler, in particular comprising a hollow body, especially a container, a vial, a syringe, and/or a hollow tube.

The sampler can be configured to be hermetically sealed or the sampler can be configured to be a non-hermetically closed device.

According to a preferred embodiment, the sampler comprises a heatable container for receiving a sample, an inlet for introducing a gaseous fluid into the inside of the container and an outlet for retrieving a gaseous fluid from the sampler.

In particular, the container comprises an opening for inserting the sample, especially a cork stopper, into the container.

Thereby, preferably, an edge of the opening is configured to enclose the sample in a given contact area, when the sample is placed in the container. With such a container, it is for example possible to use the sample, e.g. a cork stopper for closing the container. Thus, no additional closure is required in this case which can be advantageous for automated screening applications. Nevertheless, other configurations are possible as well.

For example, the container can also have a plug and/or a moveable closure, e.g. a plunger and/or a piston, which allows for closing the container and/or the opening. In this case, the container can e.g. be a syringe-type container and/or a syringe.

With a moving closure it is for example possible to push analytes extracted from the sample out of the container. Also, a sample, e.g. a cork stopper, can be placed in the container which is closed with the movable closure and which can optionally be prefilled with a carrier gas, such that analytes extracted from the sample, preferably by evaporation, are accumulated in the container before introducing them into the ion molecule reactor. Subsequently, the fluid, especially the gaseous fluid, surrounding the cork stopper and comprising the extracted analytes can be pushed out of the container with the moveable closure, e.g. a plunger and/or a piston. This allows for extracting the sample fluid without further dilution and maintaining a defined flow rate and/or pressure.

According to a further preferred embodiment, the container and/or the opening is configured such that there is a free passage between the container and/or the opening when the sample is placed in the container and/or when the container is put over the sample. In this case, preferably, the free passage can for example be used as an overpressure drain.

Moreover, especially, the container and/or the opening is configured not to touch the sample, especially a cork, when the sample is placed in the container and/or when the container is put over the sample. For example, the container can be a unilaterally end-closed tubular container having a free opening on the opposite side. In such an embodiment, preferably, the opening is larger than the sample to be introduced. With such a setup, the container does not touch the sample, especially a cork, that is analysed. Thus, carry-over and/or memory effects in the container from one to the next sample can be prevented.

Preferably, the sampler comprises a heating element which allows for heating the container, especially to a temperature of 20-300° C., preferably 30-100° C., in particular to 40-75° C. The heating element can be an integrated heating element, which is for example integrated in the container. Additionally or alternatively, an external heating element can be used. Preferably, an external heating element can be coupled to the container and decoupled from it with a mechanical interface. E.g. the heating element comprise or consist of heating wires, an induction heater, a microwave source and/or an infrared source.

With a heating element, it is possible to heat up a sample in the sampler causing evaporation of analytes comprised in the sample. However, it might also be possible to effect evaporation of analytes without a heating element, e.g. by reducing the pressure in the sampler.

Especially preferred, the sampler comprises a heat exchanger element for pre-heating a gaseous fluid before entering the inlet, whereby, preferably, the heat exchanger element allows for contacting the gaseous fluid with an outside surface of the container before entering the inlet. In this case, if the container is heated to a certain temperature, gaseous fluids can be heated up to the temperature of the container in an efficient and reliable manner.

If the sampler comprises a container, the container preferably comprises or consists of a unilaterally end-closed tubular container, especially with the outlet in an end face and/or with the inlet in a lateral surface of the unilaterally end-closed tubular container. Preferably, the inlet is located in a region of the open end of the unilaterally end-closed tubular container. Preferably, the tubular container is of cylindrical shape, especially circular cylindrical shape.

However, the container can in principle be of any shape. E.g. the container can have the shape of a prism, e.g. with triangular or rectangular base.

The inlet preferably is a ring-shaped or ring segment-shaped slit in a lateral surface of the unilaterally end-closed tubular container. The outlet is in particular a central bore in the closed end face of the container.

With such embodiments, a sample can easily be introduced through the open end of the unilaterally end-closed tubular container whereas the inlet and the outlet are maximally spaced apart. Overall, such a configuration helps to best mix analytes evaporated from the sample in the container with a gaseous fluid, e.g. a carrier gas, which is introduced via the inlet before it leaves the container via the outlet.

Especially, the unilaterally end-closed tubular container is comprised within a spaced apart tubular encasing, such that there is an enclosed and free volume around the lateral surface of the unilaterally end-closed tubular container and, preferably, such that the open end of the unilaterally end-closed tubular container remains freely accessible from the outside.

In particular, the spaced apart tubular encasing comprises an opening for introducing a gaseous fluid into the free volume around the lateral surface of the unilaterally end-closed tubular container from the outside of the sampler.

Thereby, preferably, the inlet for introducing a gaseous fluid into the inside of the container communicates with the free volume around the lateral surface of the unilaterally end-closed tubular container.

With a spaced apart tubular encasing, it is possible to pre-heat a gaseous fluid before entering the inlet via the container in a very efficient manner and without need of an additional heating stage. Hence, such a configuration represents a highly beneficial heat exchanger.

However, it is for example possible to provide a gaseous fluid that has been pre-heated before with an external pre-heating stage.

Preferably the container comprises an overpressure drain, an air permeable section and/or an air permeable closure. An air permeable section and/or an air permeable closure can e.g. be made of a frit material and/or a sintered metal. Also the permeable section and/or an air permeable closure can be a perforated area or plate.

Especially, the overpressure drain, the air permeable section and/or an air permeable closure, allows for a steady fluid communication between the inside of the container and an outside of the sampler.

With an overpressure drain, an air permeable section and/or an air permeable closure, it is possible to collect analytes from the sample and/or heating operations under constant pressure conditions and/or und non-hermetical condition. This can be beneficial with regard to the evaporation rate of analytes from the sample.

However, alternatively, it is possible to omit an overpressure drain. In this case, collection of analytes from the sample and/or heating operations can be performed under hermetically sealed conditions.

In particular, the air permeable section and/or closure is ring-shaped element or a ring segment shaped element. Thereby, preferably, an inner diameter if the ring-shaped element or a ring segment shaped element is smaller than an inner diameter of the container.

Preferably, an air permeable section and/or closure, in particular a ring-shaped element or a ring segment shaped element, is placed inside the inlet. In a special embodiment, the air permeable section and/or closure protrudes out of the inlet towards the inside of the container. Especially, if present, a frit ring is arranged concentrically with respect to a longitudinal axis of the container.

A ring-shaped element or a ring segment shaped element, especially if it protrudes out of the inlet towards the inside of the container, can be used as a fixture for a sample, in particular if the sample is a cork stopper. Thereby the ring-shaped element or a ring segment shaped element can be configured to keep a section of the sample in a defined position in the container, e.g. by clamping.

Preferably, the sampler comprises means for holding a sample and/or means for releasing a sample from the sampler. As mentioned above, this can be achieved e.g. with a ring-shaped element or a ring segment shaped element. However, other means can be foreseen as well such as e.g. mechanical clamps, fasteners, locks and the like.

According to another preferred embodiment, the kit of parts or the arrangement furthermore comprising a sampling unit, in particular an automated sampling unit, which is capable of sequentially loading a plurality of samples into the sampler. Preferably, a first sample can be loaded into the sampler, then at least one analyte is collected from the first sample and subsequently, the at least one analyte is introduced into the reaction volume of ion molecule reactor. The first sample is unloaded from the sampler and a next sample is loaded into the sampler and so on.

Such sampling units are especially beneficial for industrial screening applications, e.g. cork stopper screenings. However, if high throughput is not an issue or for other purposes it might be sufficient to manually load the samples into the sampler without a sampling unit.

Especially, the sampling unit comprises sampling unit comprises a conveyor, e.g. a conveyor belt, a manipulator for placing the sampler over a sample and/or a manipulator for loading a sample into the sampler.

According to another beneficial embodiment, the kit of parts or the arrangement comprises a plurality of samplers, especially a plurality of samplers as described above. In this case it is possible to load several samples in parallel into the plurality of samplers and to sequentially or simultaneously introduce the analytes collected in each of the plurality of samplers into the reaction volume of the ion molecule reactor.

Thereby, preferably, the kit of parts or the arrangement comprises a multiport valve having a plurality of valve inlets whereby each valve inlet can be connected to an individual sampler, as well as one or more valve outlets whereby at least one valve outlet can be connected to an ion molecule reactor as described above.

Also, the kit of parts or the arrangement comprises a gas conduit for connecting at least one sampler to the analyte inlet of the ion molecule reactor, in particular via a multiport valve. Thereby, the gas conduit may comprise tubes, valves and/or connection pieces.

According to a highly preferred embodiment, the sampler is configured as a sampling unit, especially an automated sampling unit, which is capable of sequentially collecting analytes from individual samples from a plurality of samples, especially solid samples, e.g. cork stoppers.

Also with regard to the sampling unit it should be noted that it can be of use independently of the other components of the ion molecule reactor, the kit of parts, the arrangements or the setups described herein. For example, the sampling unit can be used in connection with chromatography or extraction if desired.

In particular, the sampling unit comprises a sample holder with several chambers wherein each chamber is configured for receiving an individual sample. Especially, the sample holder comprises 5-500, in particular 10-150, preferably 25-100 or about 76, chambers.

In particular, the sampling unit comprises a heating unit for heating the sample holder. Preferably, the heating unit comprises a controller, a heating element and/or a temperature sensor for setting a predefined constant temperature. For example, the heating unit is configured to heat the sample holder to a constant temperature of 30-300° ° C., especially 50-200° C., in particular, 100-150° C. or about 130° C.

Preferably, each of the chambers of the sampling unit comprises an inlet and an outlet, such that a gaseous fluid flow can pass through each of the chambers. Especially, all of the inlets are arranged in a common inlet plane, whereas all of the outlets are arranged in a common outlet plane. The inlet plane and the outlet plane are in particular two different planes which are plane-parallel.

More preferably, the sample holder comprises an inlet closing member which is configured to close and open at least a part of the inlets of the chambers as well as an outlet closing member which is configured to close and open at least a part of the outlets of the chambers. Most preferably, the inlet closing member and/or the outlet closing member is configured to dynamically and/or intermittently open and close the chambers, especially such that the chambers or the samples comprised in the chambers can be kept under essentially non-hermetically sealed conditions during the entire period in which the samples are present in the chambers.

In particular, the inlet closing member and/or the outlet closing member are moveable with respect to the sample holder or vice versa, especially such that, upon a relative movement between the sample holder and the inlet closing member and/or the outlet closing member, at least a part of the inlets of the chambers and/or at least a part of the outlets of the chambers can be opened and/or closed simultaneously.

In particular, in operation, the sampling unit is configured to constantly move or rotate the sample holder with respect to the inlet closing member and/or the outlet closing member, preferably with an essentially constant velocity.

Preferably, the inlet closing member and/or the outlet closing member comprises several through openings which are arranged such that they can be brought over the inlet openings and/or the outlet openings of at least a part of the chambers. Preferably, for closing the chambers, the through openings in the inlet closing member and/or the outlet closing member can be brought over a section of the sample holder next to the inlet openings and/or the outlet openings of the chambers. In this manner, the inlets and/or outlets of chambers can be closed by the inlet closing member and/or the outlet closing member.

Especially, the inlet closing member and/or the outlet closing member only covers a first section of the sample holder whereas a second section of the sample holder is not covered by the inlet closing member and/or the outlet closing. With such a setup, the chambers of the sample holder in the second section are freely accessible, e.g. for loading or unloading the chambers.

Especially, the inlet closing member is included in a housing which allows for delivering a gaseous fluid to the inlet closing member, especially to a region of the inlet closing member facing away from the sample holder. Likewise, the outlet closing member is included in a housing which allows for discharging a gaseous fluid from the outlet closing member, especially from a region of the inlet closing member facing away from the sample holder. With this setup, a gaseous fluid can be passed through the through openings of the inlet closing member via the chambers to the through openings of the outlet closing member and then be discharged from the sampling unit.

Furthermore, it is preferred to provide channels between neighbouring chambers whereby the channels are configured to produce a curtain of a gaseous fluid between neighbouring chambers for separating the inlets and/or outlets of neighbouring chambers at least in sections. Especially, the channels are configured such that their longitudinal axes run essentially perpendicular to the longitudinal axes of the chambers. Preferably, the channels are present in the form of grooves in the common inlet plane and/or in the common outlet plane. Thereby, a longitudinal opening of the grooves can be covered with the inlet closing member or the outlet closing member, respectively.

In particular, the sampling unit comprises at least one removal station for individually retrieving analytes evaporated from a sample in a specific chamber and removing them from the sampler unit, e.g. via a sampler outlet. Especially, the sample holder is moveable with respect to the removal station or vice versa, such that individual chambers can be moved to the removal station sequentially or such that the removal station can be moved to individual chambers sequentially. Preference is given to a configuration where the sample holder is moveable with respect to a fixed removal station.

Preferably, the removal station comprises a gas inlet for introducing a carrier gas into a specific chamber of the sample holder.

According to a highly preferred embodiment, the sample holder comprises a hollow cylinder, especially a hollow circular cylinder, whereby the chambers are present in a wall of the hollow cylinder. Especially, the chambers are designed as bores, preferably with their longitudinal axes running in a direction parallel to a longitudinal axis of the hollow cylinder, preferably from one end face to the opposite end face of the hollow cylinder. However, it is also possible to provide a sample holder with a different form, e.g. with a straight body. Preferably, the bores are circular cylindrical bores.

Preferably, the sample holder, especially in the form of a hollow cylinder, is movably and/or rotatably mounted in between the inlet closing member and the outlet closing member, which preferably have through openings arranged with the same spacing as the chambers of the sample holder. Thereby, the inlet closing member and the outlet closing member preferably are mounted in a fixed position in the sampling unit. For example, by rotation the sample holder, the inlet and outlet of a chamber can be opened and closed.

Even more preferred, the sampling unit is configured such that by moving the sample holder, the through openings of the inlet closing member can be brought (i) in a first position in which the through openings of the inlet closing member are in fluid communication with the inlets of the chamber, (ii) a second position in which the through openings of the inlet closing member are in fluid communication with the channels or grooves in the common inlet plane between the chambers and (iii) a third position in which the through openings of the inlet closing member are placed next to the inlet openings and next to the channels. Likewise, the sampling unit preferably is configured such that by moving the sample holder, the through openings of the outlet closing member can be brought (i) in a first position in which the through openings of the outlet closing member are in fluid communication with the outlets of the chamber, (ii) a second position in which the through openings of the outlet closing member are in fluid communication with the channels or grooves in the common outlet plane between the chambers and (iii) a third position in which the through openings of the outlet closing member are placed next to the outlet openings and next to the channels.

Even more preferred, the sampling unit is configured such that a gas flow can be provided through the through openings of the inlet closing member. If the through openings of the inlet closing member and the outlet closing member are brought over the inlet openings or the outlet openings, respectively, of at least a part of the chambers, these chambers can be flushed with a gas. With such a setup, for example, a sample comprised in a specific chamber can be heated in a constant gas flow for a certain dwell time in order to accumulate analytes at the sample surface under homogeneous temperature conditions, before the analytes are finally removed from the chamber in the removal station.

When moving or rotating the sample holder, the flow of gas through the through openings will be directed to the portions of the sample holder next to the chambers or to the channels or grooves at the inlet side, which helps to remove analytes from the through openings of the inlet closing member. If the through openings of the outlet closing member are brought into fluid communication with the channels or grooves at the outlet side, the through openings of the outlet closing member can be cleaned. Overall, this helps to reduce or eliminate carry-over contamination between individual chambers or samples. Moreover, this position can be used to obtain a reference measurement or zero measurement.

For example, in operation, the chambers are kept under non-hermitically sealed conditions, e.g. with a gaseous fluid flowing through the chambers, for a given period whereby the inlet closing member and/or the outlet closing member are in open position. As well, at this time, analytes can be retrieved from a specific chamber being present in the removal station. Afterwards, the sample holder can move further with respect to the inlet closing member and/or the outlet closing member such that a next chamber can move to the removal station or vice versa. Thereby, the chambers can be closed by the inlet closing member and/or the outlet closing member for this chamber switching period. Typically, the chamber switching period is shorter, especially much shorter, than the period in which the chambers are in open position. Thus, although during the chamber switching period the chambers are closed or a flow of a gaseous fluid through the chambers will stop for a short period of time, the samples in the chambers of the sample holder are essentially kept under non-hermetically sealed conditions during the entire time in which the samples are present in the sample holder. Such a process in which the chambers are dynamically and/or intermittently opened and closed is in strong contrast to systems in which the samples are for example kept under hermetically sealed conditions during the heating process and only opened for retrieving the analytes accumulated during the heating period.

According to a preferred embodiment, the sample holder is made of a different material than the inlet closing member and the outlet closing member. Preferably, the sample holder is essentially made of a metal, especially of steel, in particular stainless steel, and most preferred of aluminum. This turned out to be an ideal material to keep the sample holder at a given and constant temperature. Optionally the sample holder surface can be partly or in full be coated with a different material, especially with a silicon material (e.g. SilcoNert®), in particular with a plastic material preferably a polymeric material, most preferably a fluoropolymeric material for example polytetrafluoroethylene (PTFE). Such coatings are chemically highly stable against many substances. The inlet closing member and/or the outlet closing member preferably is made of a plastic material, especially a polymeric material, most preferably a fluoropolymeric material for example polytetrafluoroethylene (PTFE). PTFE can withstand rather high temperatures and is chemically highly stable against many substances. This choice of materials helps to achieve a high tightness/good sealing between sample holder, inlet closing member and outlet closing, respectively. Nevertheless, it is still possible to precisely move these elements relative to each other due to the low friction. The choice of material also helps to minimize memory effects by reducing sorption of gases to the walls.

According to a further preferred embedment, the sampling unit additionally comprises a preheating station. In the preheating station, the samples can be preheated to a certain temperature before they are introduced into the chambers of the sample holder. This helps to achieve a more homogeneous temperature distribution in solid samples, especially in cork stoppers. Overall this helps to significantly increase the yield of analytes, especially when sampling cork stoppers.

Especially, the preheating station comprises a controller, a heating element and/or a temperature sensor for setting a predefined constant temperature, in particular independently of a temperature of the sample holder. For example, the preheating station is configured to heat the samples to a constant temperature of 30-300° ° C., especially 50-200° ° C., in particular, 100-150° C. or about 130° C. As a heating element, preferably a hot air generating device and/or a heating rod can be used.

In particular, the preheating station is configured such that in operation the samples are flowed around with a gaseous fluid. This helps to reduce cross-contamination of the samples.

For example, in the preheating station, the samples can be kept in individual receptacles, preferably receptacles which are open at opposing ends, such that a gaseous fluid can flow through the receptacles. Especially, the receptacles are present as hollow cylindrical bodies, in particular cylindrical pipe pieces. Such kind of receptacles are especially suitable for cork stoppers.

Preferably, the sampling unit and/or the preheating station further comprises a loading unit for placing individual samples in the chambers of the sample holder. Especially, the loading unit can comprise a conveyor belt, and/or a robotic arm, and/or a two- or three-axis manipulator, and/or an alignable feed channel, and/or an alignable guiding for transporting individual samples to the sample holder. Especially, the loading unit is synchronized with a movement of the sample holder, preferably such that individual samples can be loaded successively into the chambers of the sample holder.

Preferably, the loading unit is integrated in the preheating station, especially such that the loading unit can be kept at the same temperature as the samples. This helps to better keep the samples at a constant temperature during the overall sampling process.

According to a highly preferred embodiment, the loading unit comprises a moveable chain of interlinked receptacles, especially interlinked cylindrical pipe pieces. For example, the moveable chain comprises a series of cylindrical pipe pieces held together by links which are pivotable around the cylindrical pipe pieces. Preferably, the moveable chain comprises two types of alternating links. For example, the first type is inner links, having one or two inner plates surrounding the cylindrical pipe pieces in a central region. These inner links can alternate with the second type, the outer links, comprising two outer plates surrounding the cylindrical pipe pieces in a region of the ends of the cylindrical pipe pieces.

Preferably, for driving the moveable chain, the preheating station comprises a driven toothed wheel and optionally one or more further toothed wheels for guiding and/or redirecting the movable chain.

In particular, the loading unit is configured such that the movable chain, at least in a section, can be guided over at least one of the chambers of the sample holder, preferably such that a sample in the receptacle can be introduced into the chamber in a vertical movement, e.g. driven by gravity.

Overall a sampling unit as described above is highly beneficial since it greatly helps to increase the yield of analytes evaporated from samples. This is in particular beneficial with regard to the analysis of haloanisols in cork stoppers as described herein.

In a further preferred embodiment, the kit of parts is built up as a setup for analysing a sample, in particular a cork stopper, whereby, preferably, the sampler is connected to the analyte inlet of the ion molecule reactor.

A further aspect of the present invention is concerned with a method for generating analyte ions with an ion molecule reactor, in particular with an ion molecule reactor as described above, comprising the steps of:

a) Introducing analytes into a reaction volume of the chamber through an analyte inlet:

b) Providing reagent ions and introducing the reagent ions into the reaction volume:

c) Letting the reagent ions interact with the analytes in order to form analyte ions:

d) Optionally, guiding the reagent ions and/or the analyte ions with an ion guide along a predefined path through the reaction volume, preferably with an alternating electrical, magnetic and/or electromagnetic field:

Whereby, preferably, the analytes are introduced into the reaction volume along an inlet path into the reaction volume whereby the inlet path runs essentially along at least a first section of the predefined transit path in the reaction volume.

Thereby, steps c) and d) can take place at least partially simultaneously. Put differently, while guiding the reagent ions at least along a section of the transit path, the reagent ions can interact with analytes in order to form analyte ions.

According to a preferred method, the analytes are introduced into the reaction chamber in the form of a mixture together with at least one further chemical species, especially together with a plurality of further chemical species, especially with at least 5, 10, 100, 1,000, 10,000 or 100,000 different further chemical species. The further chemical species can be components of a complex mixture which is to be analysed and/or species of a carrier gas used to introduce the analytes into the reaction chamber. Typically, the further chemical species are volatile organic compounds, noble gas atoms and/or components of air.

Especially, the mixture is a homogeneous gaseous mixture. However, it is also possible to have a heterogeneous gaseous mixture, e.g. an aerosol.

Especially, the analytes comprise or consist of volatile organic compounds having a boiling point less than or equal to 300° C. measured at a standard atmospheric pressure of 101.3 kPa, optionally with boiling points higher than 300° C.

In particular the mixture comprises or consists of vapour containing substances evaporated from cork, especially from a cork stopper. In particular, the analytes comprise or consist of haloanisols and/or halophenols. Especially the analytes comprise or consist of at least one compound selected from the group of 2,4,6-trichloroanisole (TCA), 2,3,4,6-tetrachloroanisole (TeCA), 2,3,4,5,6-pentachloroanisole (PCA) and 2,4,6-tribromoanisole (TBA). In particular, the analytes comprise or consist of 2,4,6-trichloroanisole (TCA).

In particular, the mixture furthermore comprises a carrier gas, for example air, $N_2$ or a noble gas, e.g., Kr and/or Ar.

Particularly, a concentration of the analytes, especially haloanisols, in the mixture is 100 ppt or less, especially 1 ppt or less, in particular 0.1 ppt or less, for example 0.01 ppt or less, particularly 0.001 ppt or less.

Especially preferred, in the inventive method a pressure in the ion molecule reactor is below 100 mbar, preferably below 10 mbar, especially below 1 mbar. In such pressure ranges, the efficiency of the ionisation reaction as well as the yield of analyte ions is surprisingly high.

This allows inter alia for measuring analytes in ultra-low concentrations, e.g. concentrations in the range of a few ppq.

Although less preferred, for special purposes it is possible to carry out the inventive method with a pressure of 10 kPa or more, especially with 100 kPa or more.

In particular, the analyte ions are generated from the analytes and the reagent ions by chemical ionisation.

Especially the analyte ions are generated from the analytes and the reagent ions by proton transfer reaction (PTR). Thereby, hydronium ions are used as the reagent ions.

This has been shown to be highly beneficial in connection with the inventive method, especially in connection with analytes in the form of volatile organic compounds. However, other reagent ions can be used as well, for example reagent ions as described above in connection with the inventive ion molecule reactor.

Thus, in particular, reagent ions are chosen from $H_3O^+$, $O_2^+$, $CH_4^+$, $NH_4^+$, isobutane ions, noble gas ions, and/or $NO^+$. Nevertheless it is in principle also possible to use negatively charged reagent ions.

For example, in connection with haloanisols, it turned out that generating analyte ions from analytes by charge transfer reaction is highly beneficial. Thereby, positively charged reagent ions, such as e.g. $O_2^+$ and/or $NO^+$, especially $NO^+$, are particularly preferred.

In a special embodiment, the different reagent ions, e.g. $O_2^+$ and $NO^+$, are used simultaneously or alternately. When used alternately, the different ion sources for example be used intermittently. The different ions can be of the same polarity or of opposite polarity. Overall, using different reagent ions can be helpful to further increase the selectivity.

Thus, analyte ions are preferably generated from the analytes and the reagent ions by proton transfer reaction and/or charge-transfer reaction.

Thus, in a preferred embodiment, in particular in connection with haloanisols, the reagent ions are chosen to interact with the analytes in a charge-transfer chemical ionization reaction. In this case, the reagent ions are in particular chosen such that a population of unprotonated analyte ions ($M^+$) formed is greater than a population of protonated analyte ions ($MH^+$) formed. Thereby, preferably, the reagent ions are chosen not to interact with the analytes by proton transfer reaction.

Preferably, the analyte ions produced in the ion molecule reactor are introduced into a mass analyzer, especially a time-of-flight mass analyzer, a quadrupole mass analyzer, an ion trap analyzer, a sector field mass analyzer, a Fourier transform ion cyclotron resonance analyzer, and/or an Orbitrap.

In particular, the analyte ions are introduced into the mass analyser without further affecting the chemical and/or physical properties of the analyte ions. Especially, the analyte ions are introduced into the mass analyser without any further separation step. Preferably, the analyte ions are introduced into the mass analyser without being subjected to chromatography, extraction, ion-mobility separation, gas chromatography liquid chromatography, solid-phase microextraction and/or headspace solid-phase microextraction.

With the inventive method, no separation step is required. Nevertheless, it is possible to achieve a high sensitivity. However, for special applications, it might be an option to foresee an additional separation step.

In particular, in the ion molecule reactor, the reagent ions and/or the analyte ions are guided, focussed, accelerated and/or decelerated with an alternating electrical, magnetic and and/or an electromagnetic field within the reaction volume and/or along the predefined transit path, in particular as described above in connection with the ion molecule reactor.

Especially, a guiding field for guiding and/or focussing ions, in particular analyte ions and/or reagent ions, along the transit path is generated. This guiding field preferably is an electromagnetic field, especially a radiofrequency (RF) field, generating an effective potential confining the ions to a region along the transit path.

Preferably, a transport field is generated for accelerating and/or decelerating ions in a direction along the transit path. Preferably, the transport field is an electrical field, especially a DC field, which runs essentially along the transit path.

Especially, a rotating field is generated, in particular for setting an essentially constant energy of the ions. Preferably, the rotating field results in an ion motion orbiting around the mean flight path of the ions.

More preferable, a transport field and a guiding field is generated simultaneously. Most preferred, a rotating field is generated additionally to the transport and the guiding field. This allows for controlling the velocity of the ions along the transit path independently of the focussing and/or guiding of the ions in a highly efficient manner.

For generating these fields, electrodes, voltage generating devices and other means as described above in connection with the ion molecule reactor can be used. Also, it is preferred to perform the inventive method with an ion guide, e.g. a multipole arrangement, an ion funnel, an ion carpet or combinations thereof, as described above.

In particular, the ion molecule reactor and/or the transit path is at least partially surrounded by a tubular element, especially as described above.

In a further preferred method, a fluid is introduced into the reaction volume through at least one porous and/or gas permeable section of the tubular element.

In particular, a sheath or buffer gas is introduced into the reaction volume, e.g. in order to reduce wall or memory effects, for example due to pressure difference between inside and outside pressure of the tubular element, or for dilution of analytes. However, it is also possible to introduce a reagent gas and/or reagent ions through the at least one porous section of the tubular element into the reaction volume. In this case, the at least one porous section of the tubular element has the function of a reagent ion inlet.

According to a highly advantageous method, neutrals and/or ions having left the predefined transit path are removed out of the reaction volume and/or the ion molecule reactor through the at least one porous and/or gas permeable section of the tubular element.

Details of the tubular element as well as the at least one porous and/or gas permeable section have been described above in connection with the ion molecule reactor. Preferably, the tubular element is comprised within an outer tubular element as mentioned above.

In the following a highly preferred method for analysing a sample, especially a cork stopper, is described. The method comprising the steps of:

a) Collecting at least one analyte, especially a haloanisol, from the sample containing the at least one analyte, especially with a sampler as described above;

b) Generating analyte ions from the at least one analyte with a method as described above c) Analysing the analyte ions, especially with a mass analyser, e.g. as described above.

Preferably, in step a), the at least one analyte is collected by heating under conditions suitable for or effecting vaporizing of the at least one analyte present in the sample.

Especially, the sample is a solid sample. However, the sample can also be a liquid sample, a gaseous sample, and/or a heterogenous sample containing mixed phases.

In particular, the sample comprises cork or consists of it, especially the sample is a cork stopper, and the heating is performed under conditions suitable for or effecting vaporizing haloanisols and/or halophenols. Especially the heating is performed under conditions suitable for or effecting vaporizing 2,4,6-trichloroanisole (TCA), 2,3,4,6-tetrachloroanisole (TeCA), 2,3,4,5,6-pentachloroanisole (PCA) and 2,4,6-tribromoanisole (TBA), possibly present in the cork.

In particular the heating of the sample and/or collecting of the analytes is effected under essentially constant pressure conditions. Thus, a sampler as described above with an overpressure drain can be used.

The at least one analyte collected in step a) preferably is mixed with a carrier gas and introduced as a mixture into the reaction volume in step b). Thereby, in particular, the carrier gas is selected from $N_2$ or noble gases, e.g. Kr, Ar, and/or from purified air. The mixture is in particular conducted from the outlet of the sampler through a gas conduit system to the analyte inlet of the ion molecule reactor.

For mixing, the carrier gas preferably is directed to flow at least along a part of the surface of the sample, especially along a part of the surface of a cork stopper. This allows for taking up evaporated analytes, which might stick on the surface of the sample, within the carrier gas.

Especially, before mixing, the carrier gas is heated, preferably to a temperature suitable for effecting vaporization of the at least one analyte present in the sample. Under such conditions, risk of recondensation of analytes due to cooling or damaging analyses due to too much heat can be reduced.

Preferably, upon introducing the mixture into the reaction volume, the carrier gas is continuously provided and flows at least along a part of the surface of the sample. Thereby, analytes evaporation from the sample can be taken up continuously resulting in a well-defined stream of analytes entering the reaction volume. Thus, according to a preferred embodiment, analytes collected in step a) are continuously introduced into the reaction volume in step b) right after collection in step a).

Preferably, steps a) and b) take place in real-time. Thereby, especially, analytes collected in step a) are introduced into the reaction volume in step b) right after collection in step a). This allows for a direct analysis of the analytes in real-time. However, for special applications it is possible to first collect the analytes in step a) for a certain defined time and introduce the collected analytes at a later time into the reaction volume in step b).

In particular, the mixture comprising the at least one analyte ion is introduced into the reaction volume in step b) without further affecting the chemical and/or physical properties of the mixture. Especially, the analyte ions are introduced into the reaction volume without any further separation step. Preferably, the analyte ions are introduced into the reaction volume without being subjected to any chromatography, extraction, ion-mobility separation, gas chromatography, liquid chromatography, solid-phase microextraction and/or headspace solid-phase microextraction.

According to another preferred method, before collecting the at least one analyte in step a), the sample is heated, especially such that the samples are flowed around with a gaseous fluid, for a given dwell time. In particular, the heating comprises a preheating at a first temperature as well as main heating at a second temperature. Especially, the second temperature is higher than the first temperature. For example, the first temperature and/or the second temperature is 30-300° C., especially 50-200° C., in particular, 100-150° C. or about 130° C. This allows for accumulating analytes at the sample surface under homogeneous temperature conditions.

Especially preferred, when using a sampler which is capable of collecting analytes from a plurality of samples, such as e.g. a sampling unit as described above, a curtain of a gaseous fluid is produced between neighbouring samples in order to reduce cross-contaminations.

Especially preferred, when using a sampling unit as described above, the sample holder constantly moves and/or rotates with respect to the inlet closing member and/or the outlet closing member at least during steps a), b) and/or c), preferably with an essentially constant velocity. Thus, individual samples, e.g. cork stoppers, can be analysed successively whereas between two sample measurements, a reference measurement can be obtained.

Preferably, for collecting the analytes the samples are flowed around with a carrier gas, whereby, preferably, a flow rate of the carrier gas is higher than a flow rate of the gaseous fluid during heating.

Especially, during heating and/or when collecting the analytes, the samples are kept under a pressure higher than ambient pressure. This helps to reduce contaminations.

With the inventive method, no separation step is required. Overall, this will significantly speed up the analysis. Nevertheless, it is possible to achieve a high sensitivity. However, for special applications, it might be an option to foresee an additional separation and/or concentration step.

With the above described method for analysing a sample, in step a) a sampler and/or a sampling unit as described above is preferably used.

In particular, the sampler comprises a heatable container for receiving the sample, the container comprising an opening for inserting the sample in the container, an inlet for introducing a gaseous fluid into the inside of the container and an outlet for retrieving a gaseous fluid. The container preferably comprises an air permeable element or closure, such that an inside of the container communicates with an outside of the container and/or the outside of the sampler.

According to a preferred embodiment, the sample, especially a cork stopper, is inserted into an opening for inserting the sample in the container, whereby the sample is enclosed by the opening in a contact area. Especially, the opening of the container is selected such that it has a shape that is complementary to a shape of the sample at one end, so that the opening is closed with the sample when the sample is present in the container.

According to a further preferred embodiment, the sample, especially a cork stopper, is inserted into the container and/or the opening such that there remains a free passage between the container and/or the opening when the sample is present in the container.

Especially, the sample is inserted into the container such that it does not to touch the container and/or the opening, when the sample is placed in the container.

Most preferred, the sampler is configured as a sampling unit, especially an automated sampling unit, which is capable of sequentially collecting analytes from individual samples from a plurality of samples, especially solid samples, e.g. cork stoppers. The sampling unit in particular is configured as described above.

Another aspect of the present invention is the use of an ion molecule reactor as described above in mass spectrometry and/or with a mass spectrometer. Thereby, the mass spectrometer or a mass analyzer used for mass spectrometry is defined as described above.

Moreover, the present invention is concerned with the use of an ion molecule reactor, a kit of parts, an arrangement and/or a setup as described above for the analysis of a gaseous mixture comprising at least one analyte species and in particular at least 5, 10, 100, 1,000, 10,000 or 100,000 different further chemical species.

A further aspects of the present invention is related to the use of an ion molecule reactor, a kit of parts, an arrangement and/or a setup as described above for analyzing a cork stopper for the presence of cork taint.

Moreover, an additional aspect of the present invention concerns the use of an ion molecule reactor, a kit of parts, an arrangement and/or a setup as described above for the analysis of a sample for the presence and/or a proportion of haloanisols and/or halophenols, especially of 2,4,6-trichloroanisole (TCA), 2,3,4,6-tetrachloroanisole (TeCA), 2,3,4,5,6-pentachloroanisole (PCA) and 2,4,6-tribromoanisole (TBA), in the sample.

Also it should be noted that a tubular element comprising at least one porous and/or gas permeable section as described above can be of use independently of the other components of the ion molecule reactor described herein. For example, a tubular element comprising at least one porous and/or gas permeable section can be used instead of an ion guide according to the present invention. However, it can also be used for other applications.

Thus, another aspect of the present invention is concerned with a tubular element comprising at least one porous and/or gas permeable section, in particular for use as an ion transfer tube and/or an ion molecule reactor. Especially, the at least one porous or gas permeable section is a ring-shaped or annular section of the tubular element. In a special embodiment, the tubular element is porous and/or gas permeable along its whole length.

According to a further preferred embodiment, this tubular element comprising at least one porous and/or gas permeable section is comprised within an outer tubular element as described above. Thus, in particular, the outer tubular element is gas-tight or non-porous. For example it is made of stainless steel.

Especially, the inner diameter of the outer tubular element is larger than the out diameter of the tubular element. Thus, in this case, there is a free volume between the tubular element and the outer tubular element. This volume can e.g. be used to provide a fluid, e.g. a gas, which is to be introduced trough a porous section of the tubular element in to the reaction volume. Also it is possible to reduce the pressure within the free volume to a value below a pressure in the reaction volume in order to remove neutral analytes and/or other substances from the reaction volume, e.g. due to the pressure difference.

Preferably, the outer tubular element comprises an opening for introducing fluids and/or for evacuating the free volume between the two tubular elements.

Especially, the tubular element comprising at least one porous and/or gas permeable section comprises at least one electrode as described above. Further preferable features of the tubular element have been described above.

In particular, the tubular element comprising at least one porous and/or gas permeable section is part of an ion molecule reactor and/or a mass spectrometer.

If the tubular element comprising at least one porous and/or gas permeable is used as an ion molecule reactor, it preferably comprises a reagent ion source as described above.

In particular, the tubular element comprising at least one porous and/or gas permeable section can be used instead of an ion guide in an ion molecule reactor as described above.

Therefore, another aspect of the present invention is an ion molecule reactor for generating analyte ions from analytes, in particular for use with a mass spectrometer and/or in mass spectrometry, comprising:

a) a reaction volume in which reagent ions can interact with the analytes in order to form analyte ions, especially by chemical ionisation;

b) at least one tubular element comprising at least one porous and/or gas permeable section surrounding the reaction volume at least partially for guiding the reagent ions and/or the analyte ions along a predefined transit path through the reaction volume;

c) at least one analyte inlet which allows for introducing the analytes along an inlet path into the reaction volume, whereby a direction of the inlet path runs essentially along a direction of at least a first section of the predefined transit path in the reaction volume:

d) at least one reagent ion source and/or at least one reagent ion inlet which allows for providing reagent ions into the reaction volume.

Thereby, preferably, the at least one reagent ion source and/or the at least one reagent ion inlet is located radially outwards with respect to the first section of the predefined path, the inlet of the analytes and/or the direction of the inlet path, and is configured such that the reagent ions can be introduced into the reaction volume along at least two distinct directions and/or from at least two distinct positions.

With such a setup, a fluid can be introduced through the porous and/or gas permeable section from an outside to the inside of the tubular element. The fluid can e.g. be a reagent gas, reagent ions, a sheath gas and/or a buffer gas. In particular, if the fluid is introduced in a radial direction, the incoming fluid effectively prevents atoms and/or molecules, e.g. analytes and/or analyte ions, from reaching the inner walls of the tubular element. However, in contrast to prior art systems, no high pressure laminar flow of sheath gas is required.

Other advantageous embodiments and combinations of features come out from the detailed description below and the totality of the claims.

BRIEF DESCRIPTION OF THE DRAWINGS

The drawings used to explain the embodiments show:

FIG. 16b A cross section along line A-A of the sample holder of FIG. 16a;

In the figures, the same components are given the same reference symbols.

PREFERRED EMBODIMENTS

Figure 1:
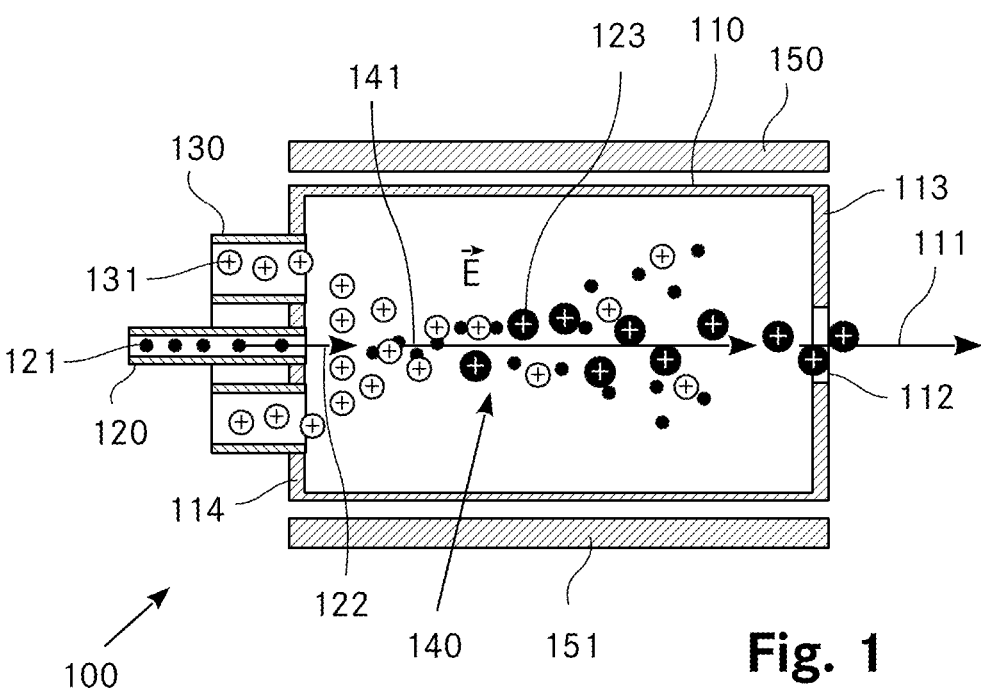
FIG. 1 A cross-section of a first ion molecule reactor with an annular reagent ion inlet around the analyte inlet and an ion guide composed of a multipole electrode arrangement.

FIG. 1 shows a cross section of a first ion molecule reactor 100. The ion molecule reactor 100 comprises a hollow cylindrical housing 110 having a longitudinal axis 111 and a reaction volume 140 inside the housing 110. Thereby, the housing 110 forms a tubular element surrounding the reaction volume. The housing is e.g. made from a doped lead silicate glass with a resistive layer on the inside. A length of the housing in longitudinal direction is for example 100 mm, an inner diameter is 10 mm and an outer diameter is 13 mm. The electrical resistance between the right axial end 113 and the left axial end 114 of the housing 110 is e.g. 1 GΩ.

At the right side in FIG. 1 the housing 110 has a circular opening 112 at the right axial end 113 being concentric with the longitudinal axis 111. The circular opening is an exit orifice, e.g. with an aperture diameter of 1 mm. In FIG. 1 at the left axial end 114, a hollow cylindrical analyte inlet 120 runs along the longitudinal axis 111 of the ion molecule reactor 100. Through the analyte inlet 120, analytes 121, e.g. volatile organic compounds, can be introduced into the reaction volume 140 along an inlet path 122. The inlet path 122 of the analytes runs along a predefined transit path 141 in the reaction volume 140 whereby the transit path 141 runs along the longitudinal axis 111 of the housing 110.

Also at the left side in FIG. 1, an annular or ring-shaped reagent ion inlet 130 is arranged concentrically around the analyte inlet 120. Thus, the reagent ion inlet 130 is located radially outwards with respect to the predefined transit path 141 and the inlet path 122. Due to the ring-shaped or annular form, reagent ions 131 can be introduced into the reaction volume 140 from essentially all of the positions on the ring-shaped opening. The reagent ions are produced in a reagent ion source, e.g. a conventional plasma discharge reagent ion source, which is not shown in FIG. 1.

In operation, analytes 121 will undergo chemical ionisation upon collisions with reagent ions 131. Thereby, charged analyte ions 123 are formed.

In order to guide the analyte ions and the reagent ions through the reaction volume 140 along the transit path 141, the first ion molecule reactor 100 comprises an ion guide which is composed of several electrodes. Specifically, the housing 110 is surrounded by a set of four cylindrical rod electrodes 150, 151 (only two electrodes are visible in FIG. 1). All of the rod electrodes 150, 151 are regularly arranged around the housing 110 in equal angular distances and run in a direction parallel to the longitudinal axis 111 of the housing 110. In operation, the four rod electrodes 150, 151 are connected to an RF generating device (not shown), where two opposite rod electrodes 150, 151 each are connected in parallel. Between neighbouring electrodes an RF-only voltage is applied, for example with a frequency of 1-10 MHz. Thereby, a multipole guiding field is generated which allows for guiding and focussing analyte ions 123 and reagent ions 131 along the transit path 141.

Additionally, between the right axial end 113 and the left axial end 114 of the housing, a voltage generating device (not shown) can be connected which allows for applying a voltage and generating a transport field (DC field) which runs in parallel to the longitudinal axis 111 of the housing 110. Thus, the housing as such acts as a further electrode. The transport field allows for accelerating and/or decelerating the ions towards the opening 112 at the right axial end.

The four cylindrical rod electrodes 150, 151 and the housing 110 together constitute an effective ion guide which allows for selectively guiding ions in the reaction volume 140 without affecting neutrals.

Figure 2:
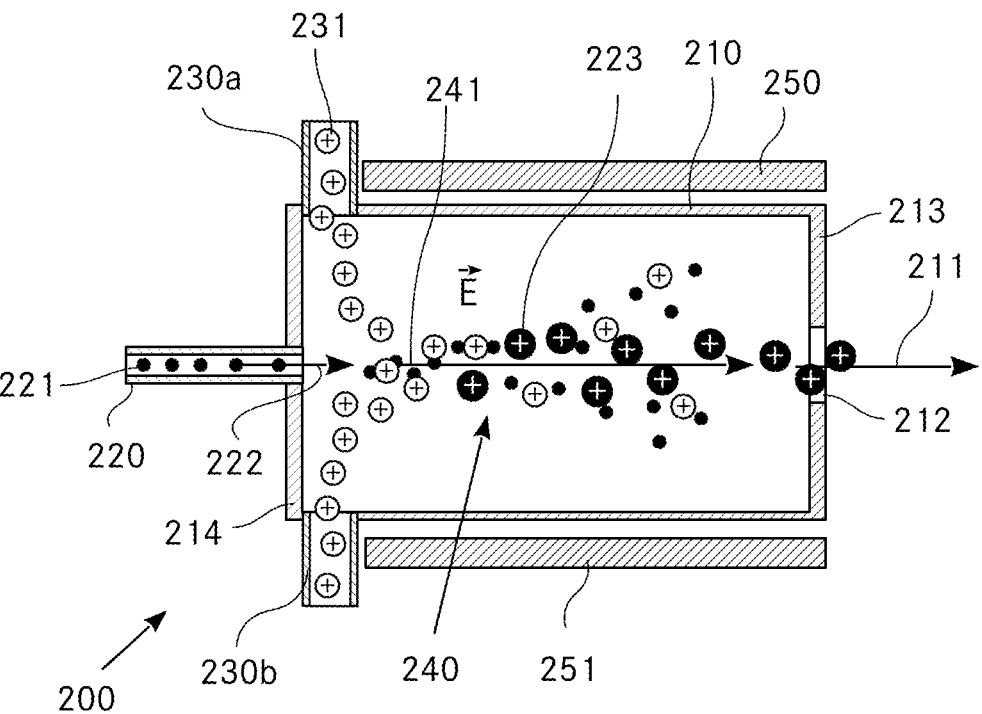
FIG. 2 A cross-section of a second ion molecule reactor with two separate reagent ion inlets mounted diametrically opposite in the cylindrical peripheral surface of a housing of the chamber and an ion guide composed of a multipole electrode arrangement.

FIG. 2 shows a cross section of a second ion molecule reactor 200. Apart from the reagent ion inlet, ion molecule reactor 200 is essentially identical with the first ion molecule reactor 100. Thus, all of the elements and parts 210, 211, 212, 213, 214, 220, 221, 222, 223, 231, 240, 241, 250 and 251 of the second reactor 200 correspond to elements and parts 110, 111, 112, 113, 114, 120, 121, 122, 123, 131, 140, 141, 150 and 151 of the first reactor 100. For example, analyte inlet 220 of the second ion molecule reactor 200 is essentially identical to analyte inlet 120 of the first ion molecule reactor 100, et cetera.

However, the second ion molecule reactor 200 does not comprise a ring-shaped reagent ion inlet which is arranged concentrically around the analyte inlet as with the first ion molecule reactor 100. Instead, the second ion molecule reactor 200 comprises two separate analyte inlets 230a, 230b which are mounted diametrically opposite in the cylindrical peripheral surface of the housing 210 at positions near the left axial end 214. Both of the two analyte inlets 230a, 230b are hollow cylindrical tubes which run in a direction orthogonal to the longitudinal axis 211 of the ion molecule reactor 200. Thus, reagent ions 231 can be introduced into the reaction volume 240 from essentially two different positions and in opposing directions, each of them essentially perpendicular to the longitudinal axis 211. Also in this case, the reagent ions 231 are produced in a reagent ion source, e.g. a conventional plasma discharge reagent ion source, which is not shown in FIG. 2.

Without being bound by theory it is believed that due to the introduction of the reagent ions from two opposing directions, the reagent ions are decelerated in front of the analyte inlet 220 by electrostatic repulsion and captured by the ion guide elements, i.e. the four cylindrical rod electrodes 250, 251 (only two of the four electrodes are shown in FIG. 2) and the housing 210.

Figure 3:
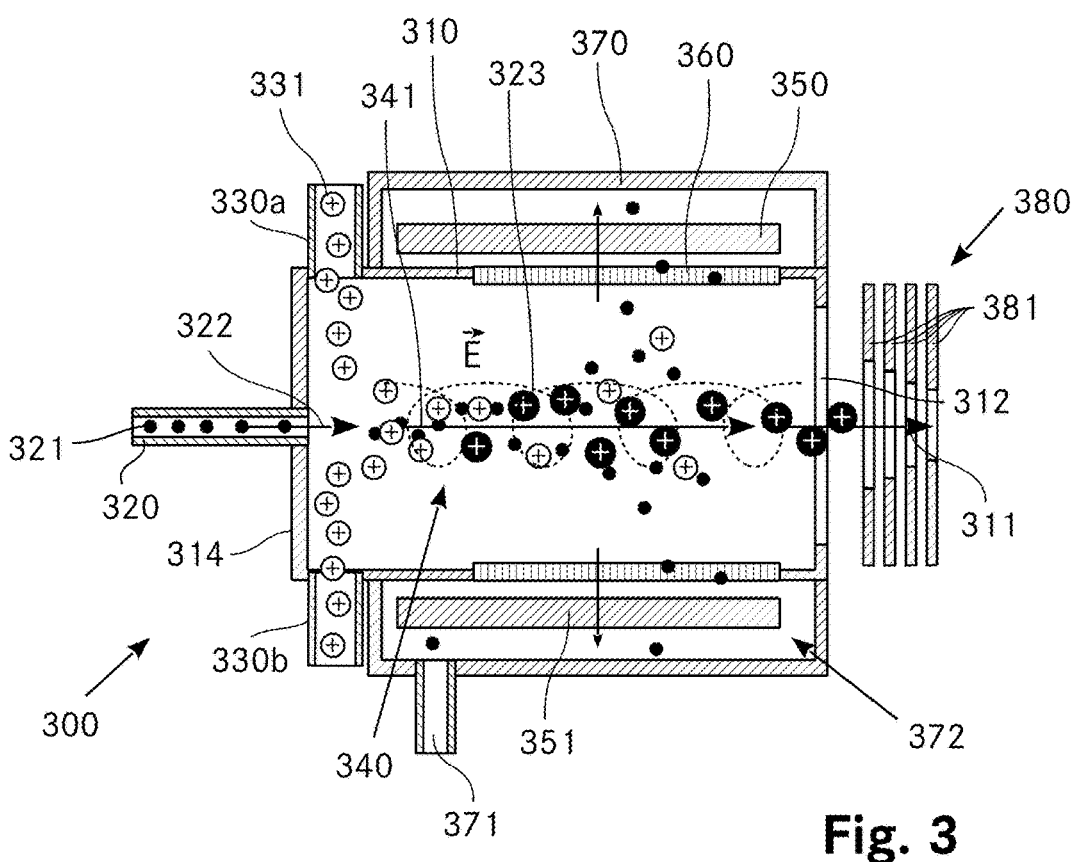
FIG. 3 A cross-section of a third ion molecule reactor with a housing comprising a gas permeable section and an out tubular element enclosing the housing in order to remove and/or introduce fluids from or into the reaction volume, respectively. Additionally, the third ion molecule reactor a multipole electrode arrangement within the ring-shaped free volume between the tubular element and the housing which in operation can generate a rotating multipole field. As well an ion funnel is arranged outside the housing where the analyte ions leave the housing of the ion molecule reactor.

FIG. 3 shows a cross section of a third ion molecule reactor 300 which is partly similar to the second ion molecule reactor 200. Specifically, all of the elements and parts 310, 311, 312, 313, 314, 320, 321, 322, 323, 330a, 330b, 331, 340, 341, 350 and 351 of the third reactor 300 correspond to elements and parts 210, 211, 212, 213, 214, 220, 221, 222, 223, 230a, 230b, 231, 240, 241, 250 and 251 of the second reactor 200. For example, analyte inlet 320 of the third ion molecule reactor 300 is essentially identical to analyte inlet 220 of the second ion molecule reactor 200, et cetera.

However, in addition to the second ion molecule reactor 200, the third ion molecule reactor 300 furthermore comprises an outer tubular element 370 of hollow cylindrical shape, which is e.g. made from stainless steel and which encloses the housing 310 concentrically over most of its length. The inner diameter of the outer tubular element 370 is larger than the outer diameter of the housing 310, such that the four rod electrodes 350, 351 are located within the ring-shaped free volume 372 between the housing 310 and the outer tubular element 370. At the outer surface of the outer tubular element 370, an opening 371 for introducing fluids and/or for evacuating the free volume 372 between the two tubular elements is mounted.

Also, the housing 310, in a section that is enclosed by the outer tubular element 370, comprises a ring-shaped and gas permeable section 360, e.g. made of a frit material. Apart from the opening 371 and the gas permeable section 360, the outer tubular element is mounted in a gas tight manner on the housing 310. Thus, the tubular housing 310 comprises a first section which is non-porous or gas tight and a second section which is porous or gas-permeable.

In operation, when evacuating the free volume 372 between the two tubular elements 310, 370, neutrals (e.g. non-ionized analytes 321) or ions having left the transit path 341, path can be removed from the reaction volume 340 and the ion molecule reactor 300 via the opening 371. Therefore, conventional vacuum pumps can be used (not shown in FIG. 3).

Figures 9, 10, 11:
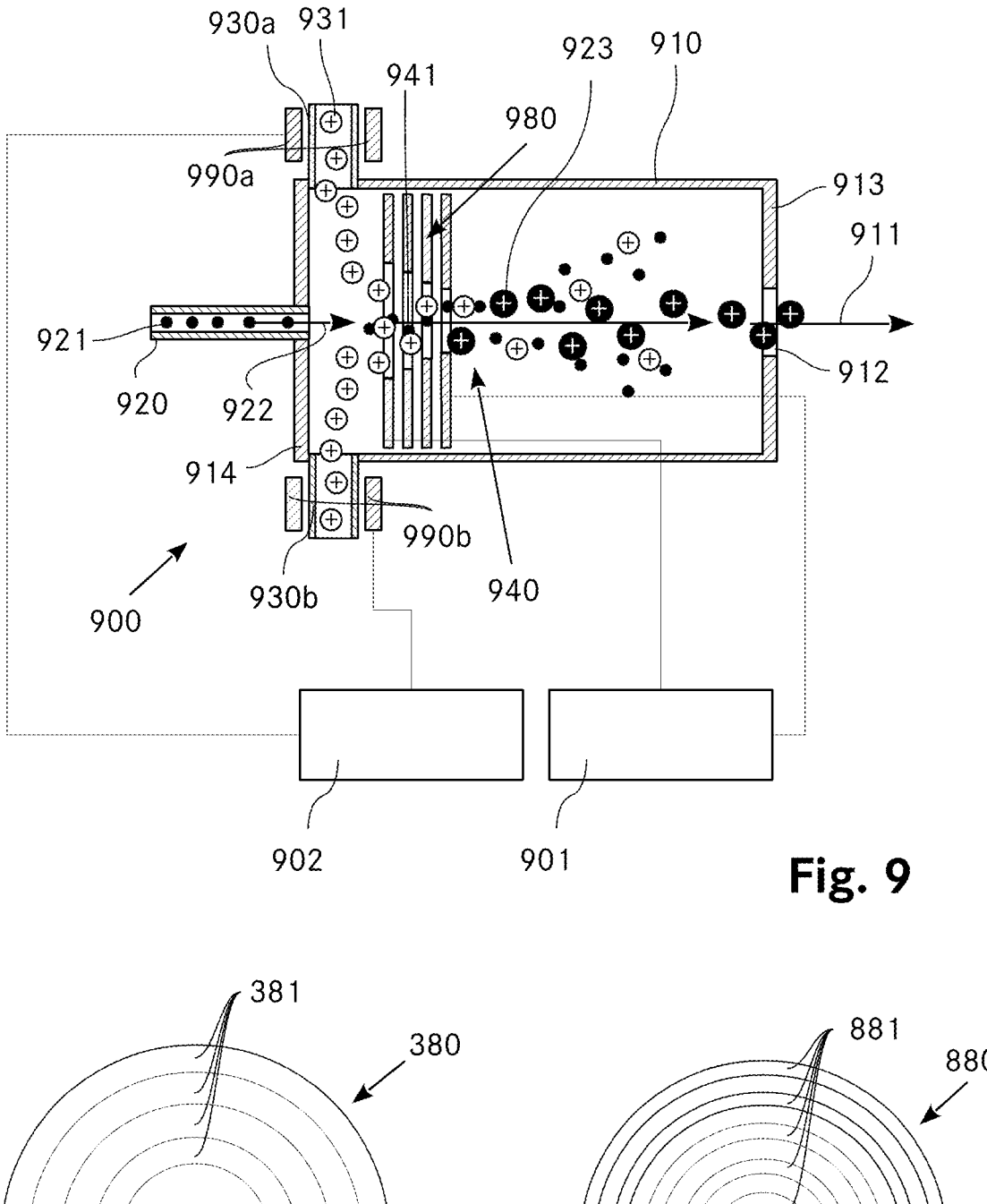
FIG. 9 A cross-section of an eighth ion molecule reactor comprising reagent ion inlets with additional guiding elements and an ion funnel as an ion guide which are connected to separate voltage generators.
FIG. 10 A top view along the longitudinal axis of the ion funnel of the ion molecule reactor shown in FIG. 3.
FIG. 11 A top view along the longitudinal axis of the ion carpet used in the ion molecule reactor shown in FIG. 8.

Additionally, the ion molecule reactor 300 comprises an ion funnel 380 which is arranged behind the opening 312 at the right axial end 313 outside the housing 310. The ion funnel 380 consists of a stack of four metallic ring electrodes 381 whose inner diameter gradually decreases. This allows for specifically extract analyte ions in a defined direction and with a high yield out of the reaction volume 340. FIG. 10 shows a top view of the ion funnel 380.

Moreover, if in operation an appropriate rotating multipole field is generated with the four cylindrical rod electrodes 350, 351, analyte ions 323 can orbit around the mean flight path in a spiral like trajectory (dashed spiral line in FIG. 3) while being transported towards the opening 312.

Figure 4:
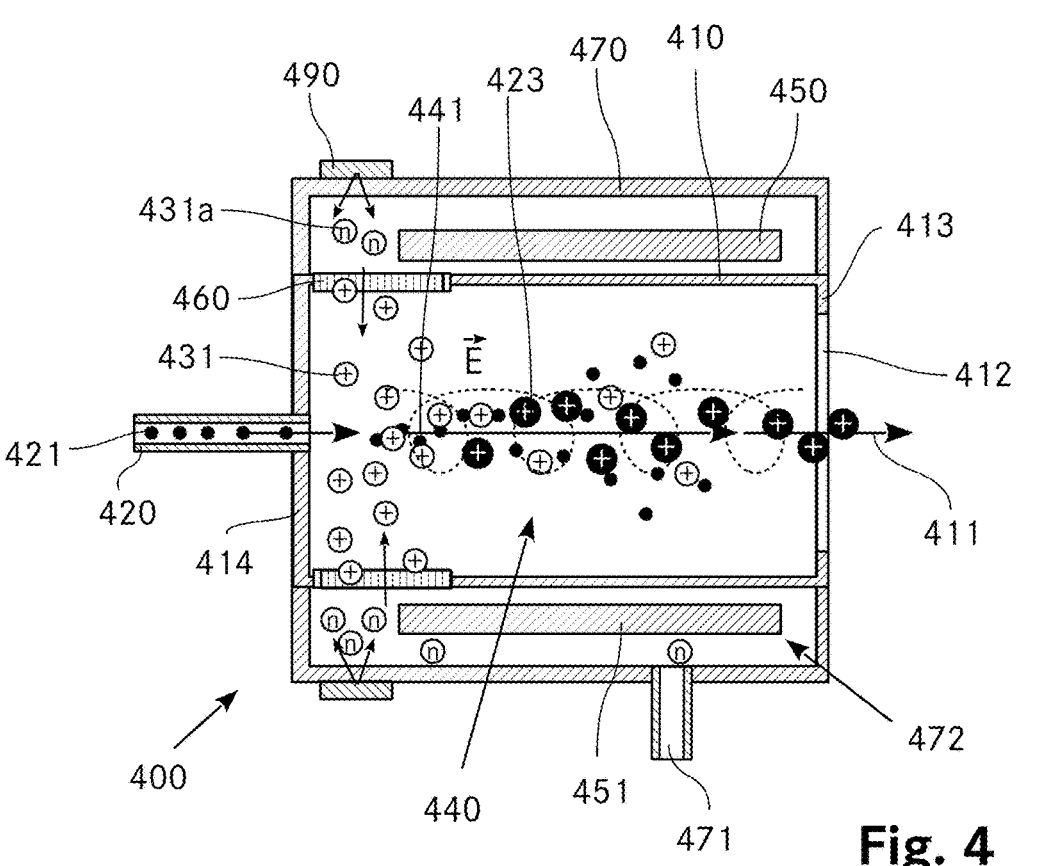
FIG. 4 A cross-section of a fourth ion molecule reactor with an ion guide composed of a multipole electrode arrangement and furthermore comprising an integrated ion-source which allows for introducing reagent ions through a gas permeable section of the housing.

FIG. 4 shows a cross section of a fourth ion molecule reactor 400 which is partly similar to the third ion molecule reactor 300. Specifically, all of the elements and parts 410, 411, 412, 413, 414, 420, 421, 422, 423, 431, 440, 441, 450, 451, 470, 471 and 472 of the fourth reactor 400 correspond to elements and parts 310, 311, 312, 313, 314, 320, 321, 322, 323, 331, 340, 341, 350, 351, 370, 371 and 372 of the third reactor 300. For example, analyte inlet 420 of the fourth ion molecule reactor 400 is essentially identical to analyte inlet 320 of the third ion molecule reactor 300, et cetera.

However, with the fourth reactor 400, there are no separate analyte inlets which are mounted diametrically opposite in the cylindrical peripheral surface of the housing. Instead, the housing 410, in a section that is enclosed by the outer tubular element 470, comprises a ring-shaped and gas permeable section 460, which is arranged close to the left axial end 414. Radially outwards, a ring-shaped x-ray source 490 is mounted on the outside surface of the outer tubular element 470.

In operation, neutral reagents 431a can be introduced into the ring-shaped free volume 472 between the housing 410 and the outer tubular element 470. Thereby, the pressure in the ring-shaped free volume 472 is chosen higher than in the reaction volume 440, such that the reagents are forced to enter the reaction volume 440 through the gas permeable section 460. In the region of the x-ray source, neutral reagents are ionized by the x-rays such that the gas permeable section 460 functions as an annular reagent ion inlet providing reagent ions from all radial directions perpendicular with respect to the longitudinal axis 411.

Figure 5:
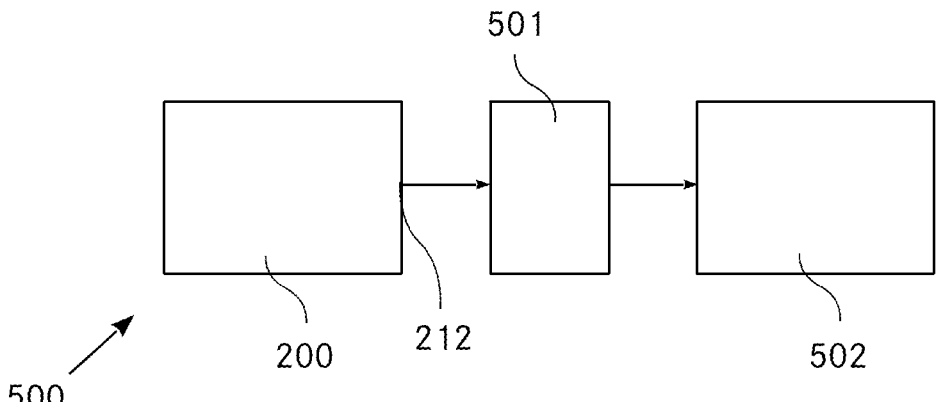
FIG. 5 A mass spectrometer setup comprising the second ion molecule reactor of FIG. 2 as well as a differential pumping stage and a mass analyzer.

FIG. 5 shows a schematic view of a mass spectrometer 500 comprising the second ion molecule reactor 200 as described with FIG. 2. Thereby, analyte ions emerging from the circular opening 212 of the ion molecule reactor are fed into an optional differential pumping interface 501 in order to further reduce the pressure and then into a mass analyzer 502, e.g. a time-of-flight mass analyzer.

Figure 6:
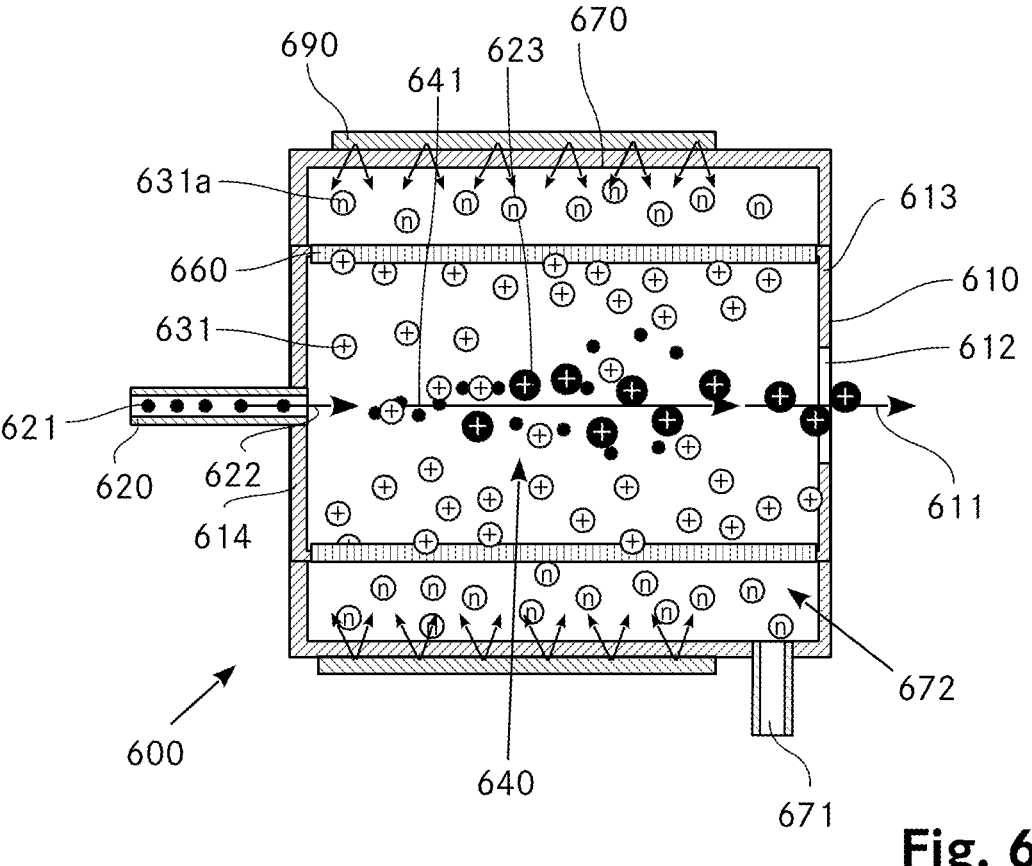
FIG. 6 A cross-section of a fifth ion molecule reactor comprising a gas permeable section along the whole length of the reaction volume.

FIG. 6 shows a cross section of a fifth ion molecule reactor 600. The ion molecule reactor 600 comprises a hollow cylindrical housing 610 having a longitudinal axis 611 and a reaction volume 640 inside the housing 610. Thereby, the housing 610 forms a tubular element surrounding the reaction volume 640. At the circular left and right end sides 613, 614, the housing is e.g. made from stainless steel while the whole curved surface area of the housing 610 is made of a ring-shaped and gas permeable section 660, e.g. a frit.

In addition, an outer tubular element 670 of hollow cylindrical shape, which is e.g. made from stainless steel, encloses the housing 610 concentrically over the complete length of the housing 610. The inner diameter of the outer tubular element 670 is larger than the out diameter of the housing 610 such that a ring-shaped free volume 672 between the housing 610 and the outer tubular element 670 is formed. At the outer surface of the outer tubular element 670, an opening 671 for introducing fluids, e.g. neutral reagent gas 631a, is mounted. Radially outwards, a ring-shaped x-ray source 690 is mounted on the outside surface of the outer tubular element 670.

At the right side in FIG. 6, the housing 610 has a circular opening 612 at the right axial end 613 being concentric with the longitudinal axis 611. In FIG. 6 at the left axial end 614, a hollow cylindrical analyte inlet 620 runs along the longitudinal axis 611 of the ion molecule reactor 600. Through the analyte inlet 620, analytes 621, e.g. volatile organic compounds, can be introduced into the reaction volume 640 along an inlet path 622. The inlet path 622 of the analytes runs along a predefined transit path 641 in the reaction volume 640 whereby the transit path 641 runs along the longitudinal axis 611 of the housing 110.

In operation, neutral reagent gas 631a is ionized by the x-ray source 690 in order to form reagent ions 631 which are introduced radially through the gas permeable section 660 into the reaction volume 640. Thereby, analytes 621 in the reaction volume 640 will undergo chemical ionisation upon collision with reagent ions 631. Thereby, charged analyte ions 123 are formed.

Due to the radial flow of reagent ions 631 the flow of analytes 621 and analyte ions 641 towards the wall or the gas permeable section 660, respectively, is reduced or inhibited.

Figure 7:
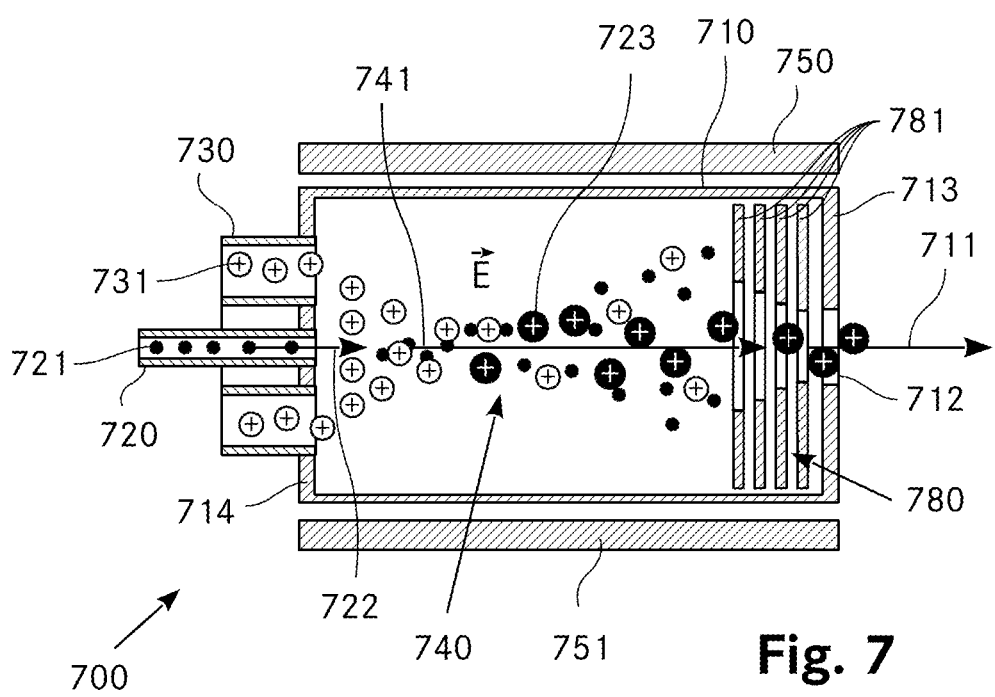
FIG. 7 A cross-section of a sixth ion molecule reactor comprising an ion guide consisting of a multipole electrode arrangement in combination with an ion funnel.

FIG. 7 shows a cross section of a sixth ion molecule reactor 700 which is similar to the first ion molecule reactor 100 shown in FIG. 1. Specifically, all of the elements and parts 710, 711, 712, 713, 714, 720, 721, 722, 723, 730, 731, 740, 741, 750 and 751 of the sixth chamber 700 correspond to elements and parts 110, 111, 112, 113, 114, 120, 121, 122, 123, 130, 131, 140, 141, 150 and 151 of the first reactor 100. For example, analyte inlet 720 of the sixth ion molecule reactor 700 is identical to analyte inlet 120 of the first ion molecule reactor 100, et cetera.

Additionally, the sixth reactor comprises an ion funnel 780 which is located inside the housing 710 in front of the right axial end 713. The ion funnel 780 comprises a stack of four metallic ring electrodes 781 and is essentially identical with the ion funnel 380 shown in FIGS. 3 and 10. The electrodes 781 of the ion funnel 780 are coaxial with respect to the transit path 741 or the longitudinal axis 711, respectively. In operation, the four ring electrodes 781 are connected to an RF generating device (not shown), whereby out-of-phase alternating RF potentials, typically with a frequency of 0.1-10 MHz, are applied to adjacent electrodes, such that charged analyte ions 723 are radially confined as they pass through the ion funnel 780.

Figure 8:
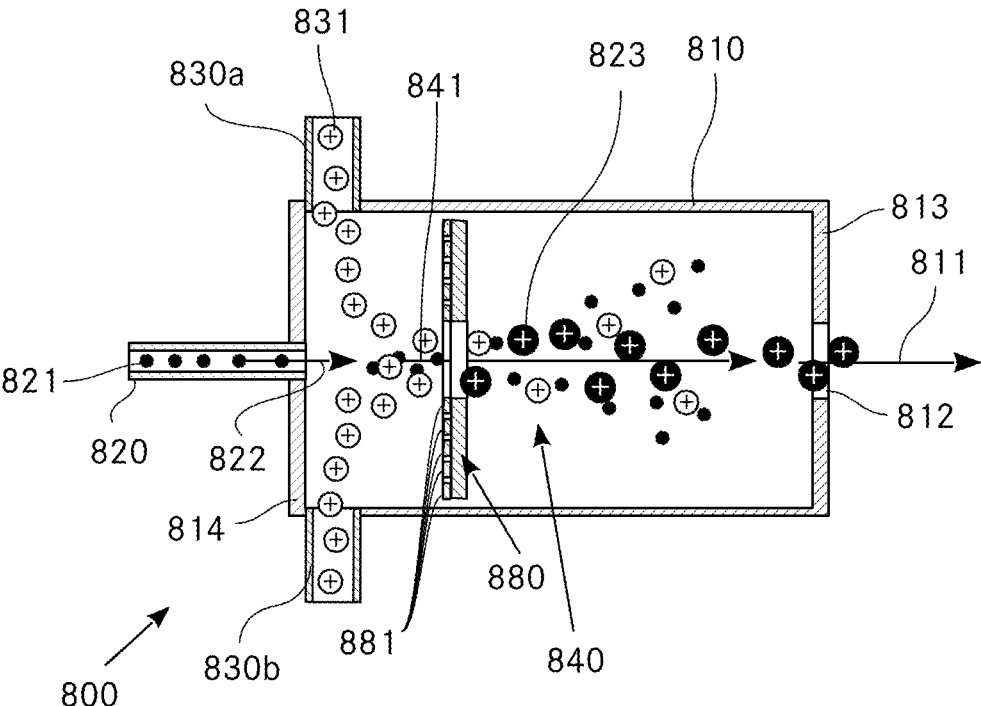
FIG. 8 A cross-section of a seventh ion molecule reactor comprising an ion guide consisting of an ion carpet.

FIG. 8 shows a cross section of a seventh ion molecule reactor 800 which is partly similar to the second ion molecule reactor 200 shown in FIG. 2. Specifically, all of the elements and parts 810, 811, 812, 813, 814, 820, 821, 822, 823, 830a, 830b, 831, 840 and 841 of the seventh reactor 800 correspond to elements and parts 210, 211, 212, 213, 214, 220, 221, 222, 223, 230a, 230b, 231, 240 and 241 of the second reactor 200. For example, analyte inlet 820 of the seventh ion molecule reactor 800 is identical to analyte inlet 220 of the second ion molecule reactor 200, et cetera.

However, the ion molecule reactor 800 does not comprise any rod electrodes. Instead, the seventh reactor 800 comprises an ion carpet 880 which is located in the reaction volume 840 close to the analyte inlet 820 and the reagent ion inlets 830a, 830b. The ion carpet 880 consists of an essentially planar arrangement of five metallic ring electrodes 881 which are mounted concentrically on an isolating support with a central orifice. The electrodes 881 as well as the central orifice of the ion carpet 880 are coaxial with respect to the transit path 841 or the longitudinal axis 811, respectively. FIG. 11 shows a top view of the ion carpet 800 along the longitudinal axis 811.

In operation, the five ring electrodes 881 are connected to an RF generating device (not shown) and a voltage is applied to the electrodes 881, such that an alternating electric field, typically with a frequency of 0.1-10 MHz, is generated which funnels reagent ions and/or analyte ions through the central orifice. Thereby, a guiding field is generated which allows for guiding and focussing analyte ions 823 and reagent ions 831 along the transit path 841. A similar device and its operation is described for example in US 2013/0120897 A1 (Amerom et al.).

FIG. 9 shows a cross section of an eighth ion molecule reactor 900 which is partly similar to the second ion molecule reactor 200 shown in FIG. 2. Specifically, all of the elements and parts 910, 911, 912, 913, 914, 920, 921, 922, 923, 930a, 930b, 931, 940 and 941 of the eighth reactor 900 correspond to elements and parts 210, 211, 212, 213, 214, 220, 221, 222, 223, 230a, 230b, 231, 240 and 241 of the second reactor 200. For example, analyte inlet 920 of the eighth ion molecule reactor 800 is identical to analyte inlet 220 of the second ion molecule reactor 200, et cetera.

However, the ion molecule reactor 900 does not comprise any rod electrodes inside the housing 910. Instead, the eighth reactor 900 comprises an ion funnel 980 which is located in the reaction volume 940 close to the analyte inlet 920 and the reagent ion inlets 930a, 930b and which is arranged coaxially with respect to the longitudinal axis 911. The ion funnel 940 consists of four ring electrodes and is essentially identical to ion funnels 380, 780 shown in FIGS. 3, 7 and 10 and is also operated in a similar manner.

Moreover, with the eighth ion molecule reactor 900, each of the regent ion inlets 930a, 930b comprises a guiding element 990a, 990b for guiding the reagent ions 931 before entering the reaction volume 940. The guiding elements 990a, 990b consist for example of four rod electrodes which are regularly arranged around the reagent ion inlets 930a, 930b. Thereby, opposing electrodes are connected in parallel whereas between neighbouring electrodes an RF-only voltage, typically with a frequency of 0.1-10 MHz, is applied. Thereby, a multipole guiding field is generated which allows for guiding and focussing reagent ions 931 before entering the inner volume of the housing 910 or the reaction volume 940, respectively.

For applying appropriate voltages to the ion funnel 980, a first voltage generating device 901 with an RF voltage and a DC voltage output is connected to the electrodes of the ion funnel 980. A further voltage generating device 902 is connected to the guiding elements 990a, 990b which allows for supplying appropriate voltages to the guiding elements 990a, 990b.

Figure 12:
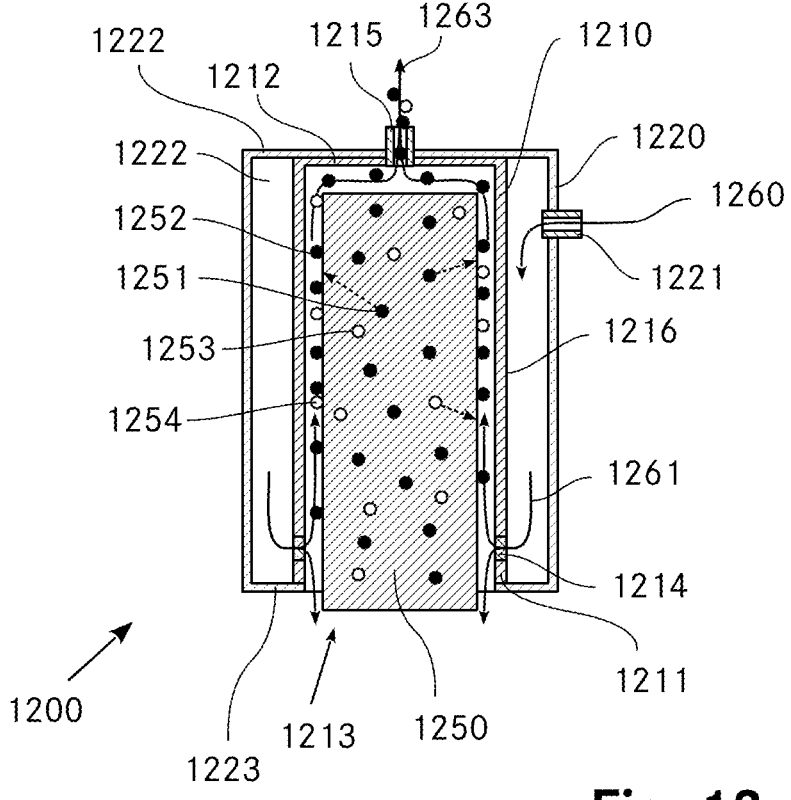
FIG. 12 A cross sectional view along a longitudinal axis of a headspace sampler for cork stoppers.

FIG. 12 shows a cross sectional view along a longitudinal axis of a headspace sampler 1200. The sampler 1200 comprises a hollow cylindrical container 1210 with a circular base area. Apart from an outlet opening in the form of a short connecting piece 1215 with a central bore, the upper end face side 1212 of the container 1210 is closed while the opposite lower end face of the container 1210 has a central and circular opening 1213. Close to the lower end face 1213, a frit ring 1214 is embedded within the lateral cylinder wall of the container 1210. Thereby, the frit ring 1214 is arranged concentrically with respect to a longitudinal axis of the container 1210.

The frit ring 1214 is made of an air permeable frit material which allows for a fluid communication through the wall of the container 1210.

Apart from the frit ring 1214, the sampler 1200 is for example made of stainless steel.

The container 1210 is comprised within a spaced apart tubular cylindrical encasing 1220, such that there is an enclosed, ring-shaped free volume 1224 around the lateral surface 1216 of the container 1210. The short connecting piece 1215 of the container 1210 extends through the upper end face 1222 of the encasing 1220. The lower end face 1223 of the encasing has a central and circular opening which is of the same size as the circular opening 1213 of the container 1210. In a lateral wall of the encasing 1220, an inlet in the form of a short connection piece 1221 is provided which allows for introducing a fluid into the free volume 1224 between container 1210 and encasing 1220. Inside the free volume 1224, a fluid can be heated up by the lateral surface 1216 of the container 1210 which in turn can be heated by the lateral surface 1216 of the container 1210. Thus, the arrangement represents a heat-exchanger element.

As also shown in FIG. 12, a cork stopper 1250 of circular cylindrical shape with a diameter smaller than the inner diameter of the container 1210 can be partly placed inside the container 1210 through the opening 1213. The cork stopper 1250 does not contact any elements of the sampler 1200 and between cork stopper 1205 and container 1210 there is a free passage such that the inside of container freely communicates with an outside of the sampler 1200. Hence, with this non-hermetically closed arrangement, an overpressure drain is realized.

In operation, the container can be heated with a heating element (not shown), which is for example embedded inside the wall of the container 1210, to an elevated temperature of e.g. 150° C. Thereby, analytes 1251, such as TCA, and possibly at least some further species 1253 comprised in the cork stopper 1250 are evaporated (indicated by dashed arrows) and concentrated in the form of gaseous analytes 1252 and further gaseous species 1254 around the outer surface of the cork stopper 1250.

Simultaneously a carrier gas 1260, e.g. $N_2$, is delivered through the connection piece 1221 inside the free volume 1224 where, the carrier gas 1260 is heated up by the lateral surface 1216 of the container 1210. The heated carrier gas 1261 then enters the inside of the container 1210 through the frit ring 1214, moves along the surface of the cork stopper 1250 inside the container 1250 whereby the gaseous analytes 1252 and further gaseous species 1254 are mixed with the heated carrier gas 1261 and transferred towards the outlet or the short connection piece 1215. Any overpressure of the carrier gas 1261 or any overpressure inside the container 1210, respectively, will automatically be released thanks to the free passage in the region of the lower end face side 1211 of the container 1210.

Thus, a gaseous mixture 1263 consisting of heated carrier gas 1263, analytes 1252 and further species 1254 exits the short connection piece 1215 of the sampler 1250.

Figure 13:
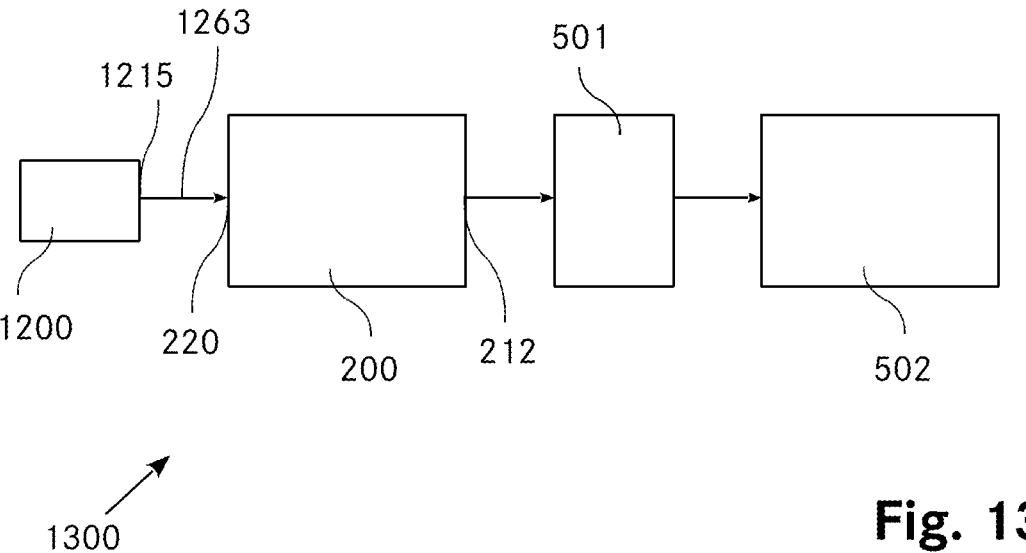
FIG. 13 A schematic view of the headspace sampler of FIG. 12 connected to the setup shown in FIG. 5.

FIG. 13 shows a schematic view of the sampler 1200 of FIG. 12 connected to the setup shown in FIG. 5. Specifically, the gaseous mixture 1263 exiting the outlet 1215 of the sampler 1200 is introduced into the second ion molecule reactor 200 shown in FIG. 2 via analyte inlet 220. Thereby, the gaseous mixture 1263 represents the analytes 221 shown in FIG. 2.

Upon chemical ionisation in ion molecule reactor 200, analyte ions and ions of further species are then produced in the second ion molecule reactor 200 whereby for analysing haloanisols (e.g. TCA) in cork stoppers, it is preferred to use $NO^+$ as reagent ions 231. Preferably, a pressure in the ion molecule reactor 200 is 1-5 mbar.

Analyte ions and ions of further species emerging from the circular opening 212 of the ion molecule reactor are fed into an optional differential pumping interface 501 in order to further reduce the pressure and then into a mass analyzer 502, e.g. a time-of-flight mass analyzer.

Figure 14:
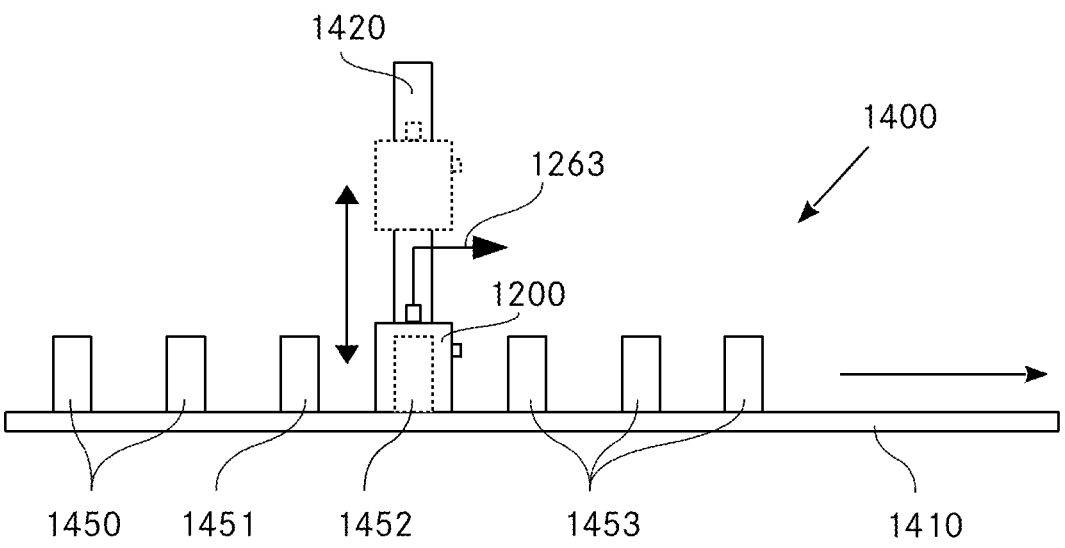
FIG. 14 A schematic view of an automated sampling unit for analysing cork stoppers. With the unit, cork stoppers can stepwise be moved on a conveyor belt whereby a sampler is sequentially placed over a cork stopper to be analysed with a linear manipulator.

In FIG. 14, a schematic view of an automated sampling unit 1400 is shown. The sampling unit comprises a conveyor belt 1410 which can be loaded with cork stoppers 1450, 1451, 1452, 1452 and which can be moved stepwise towards the right side in FIG. 14. A sampler 1200 is mounted on a linear manipulator 1420 that is capable of moving the sampler 1200 up and down in order to place the sampler 1200 over a cork stopper and subsequently remove the sample from the cork stopper.

In FIG. 14, the sampler 1200 is show in a position over a specific cork stopper 1452 which is to be analysed. Thereby, a gaseous mixture 1263 comprising inter alia the analytes of interest are for example delivered to an ion molecule reactor as explained in FIG. 13.

Once the analysis of this specific cork stopper 1452 is finished, the manipulator 1420 will move the sampler 1200 up into a hold position (indicated by dashed lines). When the sampler 1200 is in hold position, the conveyor belt 1410 will move to the right, such that the next cork stopper 1451 to be analysed is placed below the sampler 1200. Thereby, the cork stopper 1452 will be moved to the right side in FIG. 14 where further cork stoppers 1453 already analysed are located.

Then, the manipulator 1420 moves the sampler 1200 down, so that the next cork stopper 1451 can be analysed. Subsequently, the remaining cork stoppers 1450 can be treated in the same manner.

Thus, the sampling unit 1400 is configured to collect at least one analyte from each sample and to sequentially introduce the at least analyte from each sample into the reaction volume of ion molecule reactor.

Figure 15:
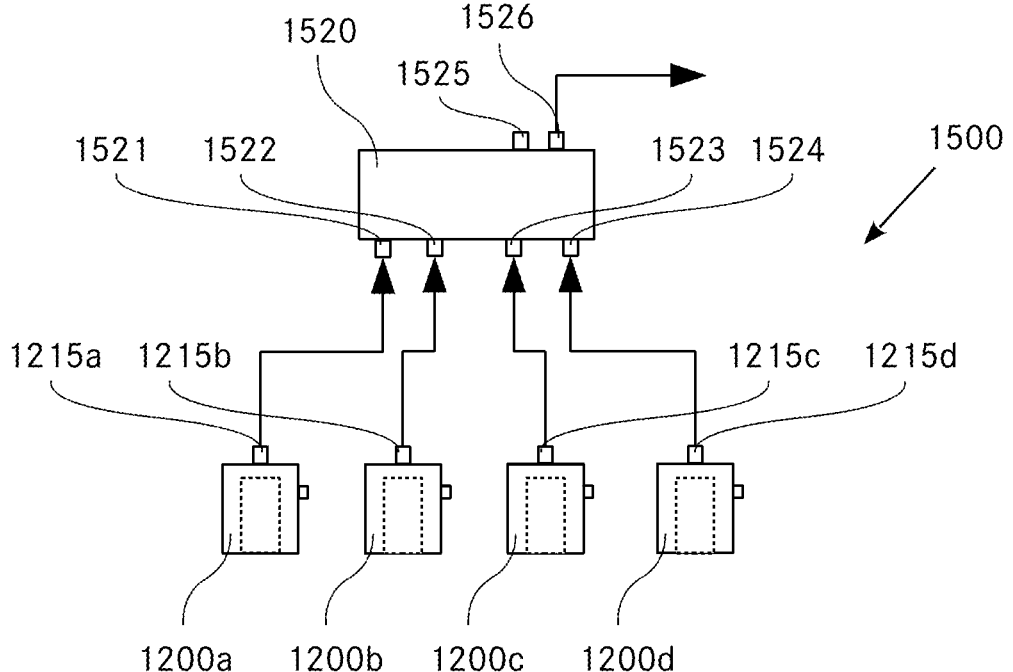
FIG. 15 A setup with four of the samplers shown in FIG. 12 connected to a multiport valve for switching between the individual samplers.

FIG. 15 shows a setup 1500 with four samplers 1200*a*, 1200*b*, 1200*c*, 1200*d* and a multiport valve 1520 comprising four valve inlets 1521, 1522, 1523, 1524 and two valve outlets 1525, 1526. All of the samplers 1200*a*, 1200*b*, 1200*c*, 1200*d* are identical in construction with the sampler 1200 shown in FIG. 12. Each one of the four samplers 1200*a*, 1200*b*, 1200*c*, 1200*d* is connected with its outlet 1215*a*, 1215*b*, 1215*c*, 1215*d* to one of the four valve inlets 1521, 1522, 1523, 1524 via a gas conduit.

With the multiport valve 1520 it is possible to sequentially analyse samples previously placed in the samplers 1200*a*, 1200*b*, 1200*c*, 1200*d* by internally connecting each of the valve inlets 1521, 1522, 1523, 1524 to the valve outlet 1526, which in turn can be connected to an ion molecule reactor. A second outlet 1526 of the multiport valve 1526 can e.g. be used for flushing the multiport valve and the samplers.

Thus, with the multiport valve 1520 it is possible to load several samples in parallel into the plurality of samplers 1200*a*, 1200*b*, 1200*c*, 1200*d* and to sequentially or simultaneously introduce the analytes collected in each of the plurality of samplers into an ion molecule reactor.

Figure 16A:
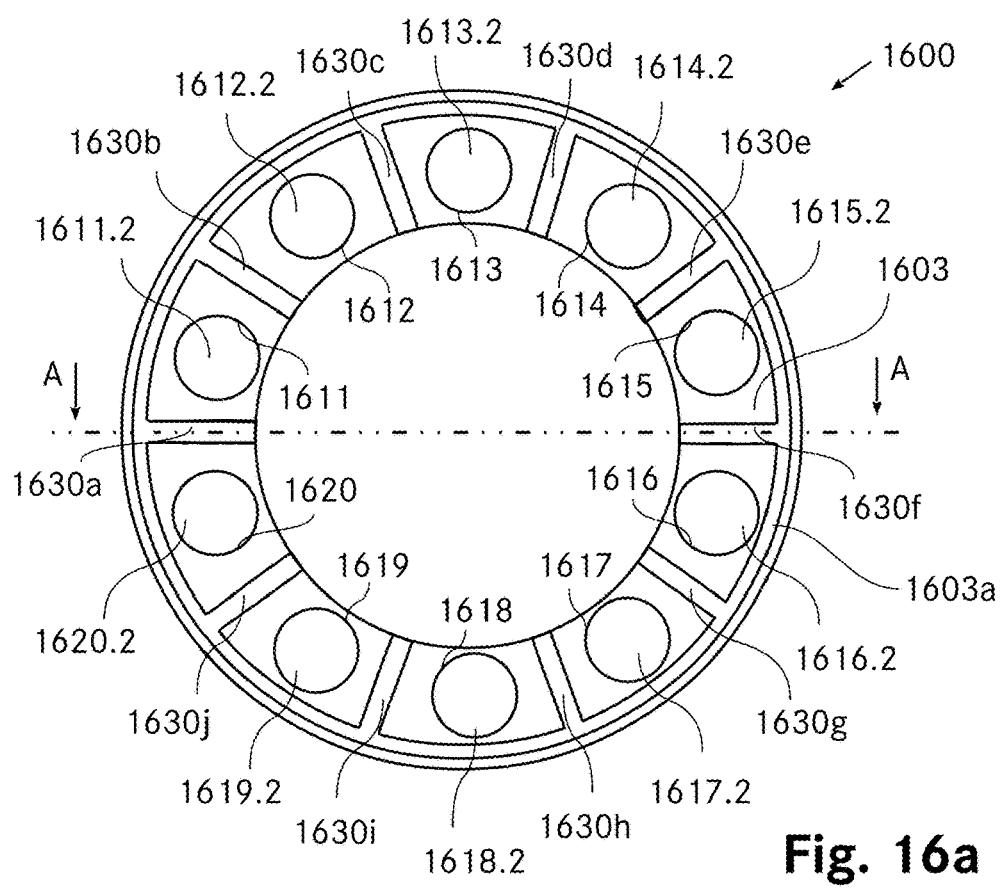
FIG. 16a A sample holder comprising several chambers for receiving a plurality of samples in a top view.
Figure 16B:
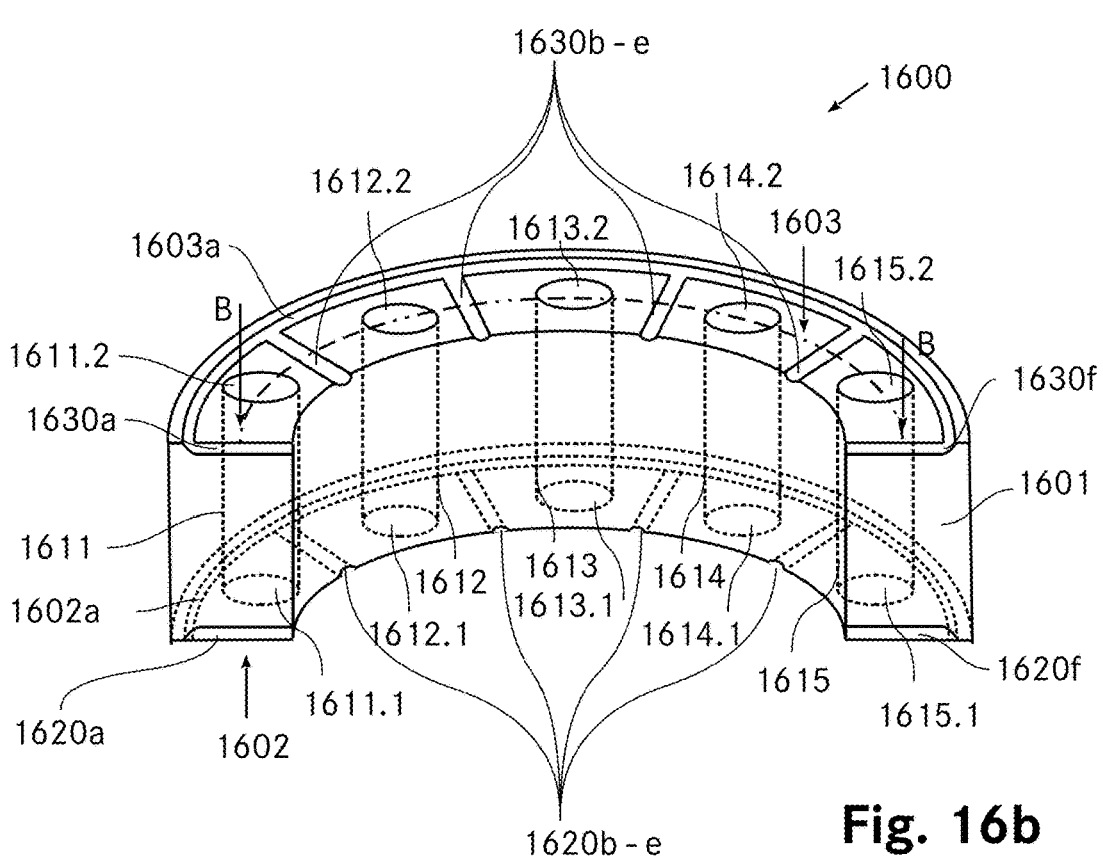

FIG. 16*a* shows a sample holder 1600 which is can be used in a sampling unit in a top view whereas FIG. 16*b* show a cross section through the sample holder 1600 along the line A-A in FIG. 16*a*.

The sample holder 1600 consists of a hollow circular cylinder 1601 with 10 regularly spaced chambers 1611, 1612, 1613, 1614, 1615, 1616, 1617, 1618, 1619, 1620 which are designed as cylindrical bores with longitudinal axes running in a direction parallel to the longitudinal axis of the hollow circular cylinder 1601 from the lower end face 1602 to the upper end face 1603 of the hollow circular cylinder 1601. Each of the chambers 1611-1620 has an inlet 1611.2, 1612.2, 1613.2, 1614.2, 1615.2, 1616.2, 1617.2, 1618.2, 1619.2, 1620.2 in the upper end face 1603 and an outlet 1611.1, 1612.1, 1613.1, 1614.1, 1615.1 (the outlets of chambers 1616, 1617, 1618, 1619 and 1620 are not shown in FIGS. 16*a* and 16*b*) in the lower end face 1602. The hollow circular cylinder 1601 is e.g. made of aluminum.

Between the inlets 1611.2-1620.2 of the chambers 1611-1620, there are 10 regularly spaced stopped grooves 1630*a*, 1630*b*, 1630*c*, 1630*d*, 1630*e*, 1630*f*, 1630*g*, 1630*h*, 1630*i*, 1630*j* present in the upper end face 1603 which begin in a radially outward region of the upper end face 1603 and runs in radial direction towards the inner edge of the upper end face 1603. Similarly, between the outlets 1611.1-1620.1 of the chambers 1611-1620, there are 10 regularly spaced stopped grooves 1620*a*, 1620*b*, 1620*c*, 1620*d*, 1620*e*, 1630*f* (groves between chambers 1616/1617, 1617/1618, 1618/1619, and 1619/1620 are not shown in FIGS. 16*a* and 16*b*) present in the lower end face 1602 which begin in a radially outward region of the upper end face and runs in radial direction towards the inner edge of the upper end face 1602.

As shown in FIGS. 16*a* and 16*b*, there is a circular groove 1603*a* surrounding the inlets 1611.2-1620.2 of the chambers 1611-1620 in the upper end face 1603. The circular grove 1603*a* interconnects all of the stopped grooves 1630*a*-1630*j* at their radially outward ends such that a gaseous fluid can be fed from the circular groove 1603*a* into the stopped grooves 1630*a*-1630*j*. Similarly, there is a circular groove 1602*a* surrounding the outlets 1611.1-1620.1 of the chambers 1611-1620 in the lower end face 1602. The circular grove 1602*a* interconnects all of the stopped grooves 1620*a*-

1620*j* such that a gaseous fluid can be fed from the circular groove 1602*a* into the stopped grooves 1620*a*-1620*j*.

Figures 17A, 17B:
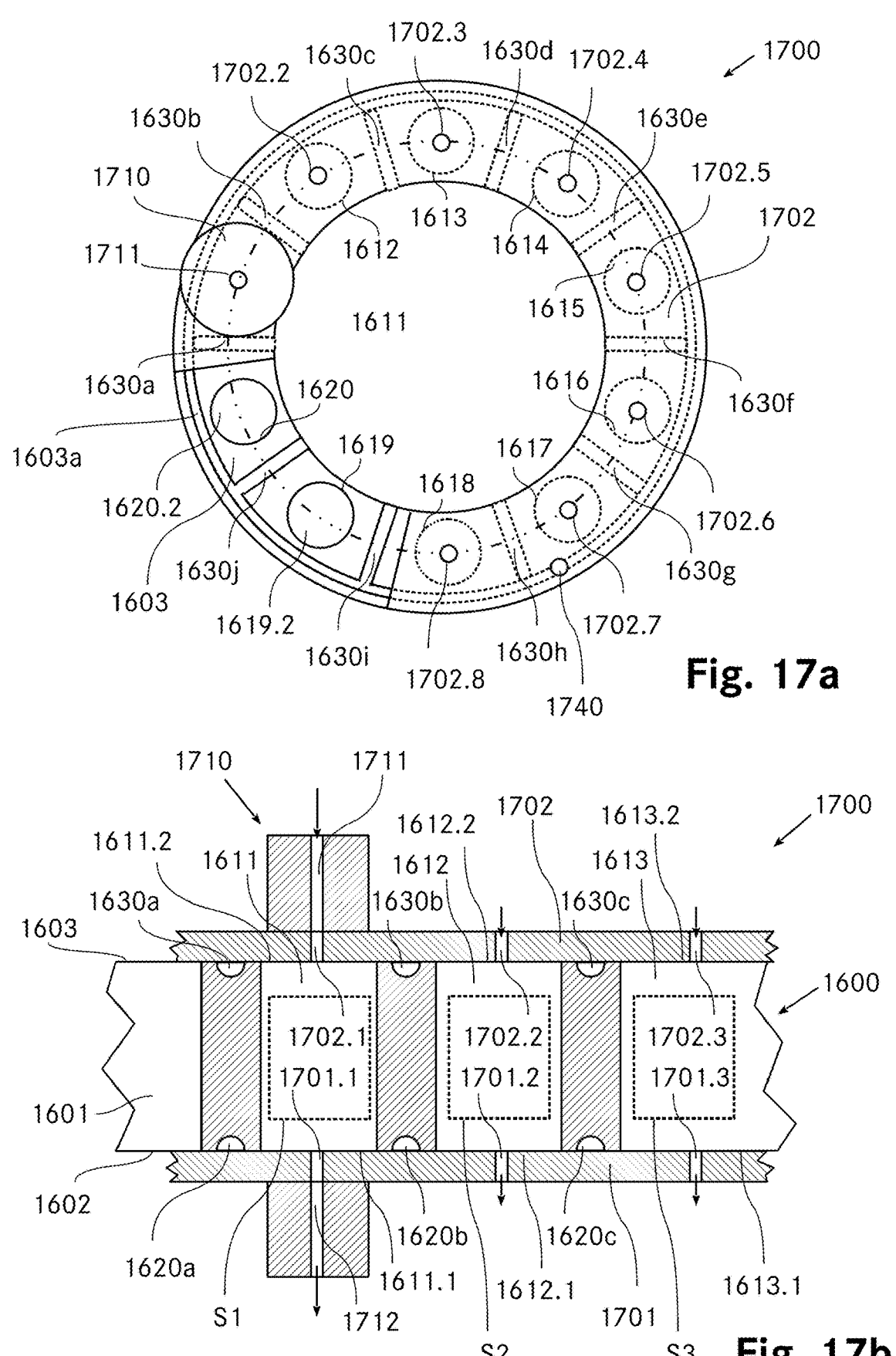
FIG. 17a An arrangement comprising a removal station for removing analytes from a specific chamber and the sample holder of FIG. 16a whereby, a part of the chambers are covered with an inlet closing member and an outlet closing member (not visible in FIG. 17a) in a top view.
FIG. 17b A detail of the arrangement of FIG. 17a in a cross-sectional view along the dashed line in FIG. 17a, whereby through openings in the inlet closing member and the outlet closing member are placed centrally over the chambers such that they are open at both ends.

FIG. 17*a* shows an arrangement comprising the sample holder 1600 of FIG. 16*a* in a top view, whereas FIG. 17*b* shows a detail of the arrangement 1700 in a cross section sectional view along the dashed line in FIG. 17*a*. Thereby, on top of the upper end face 1603, an inlet closing member 1702 which covers chambers 1611-1618 is arranged (chambers 1619 and 1620 are not covered). The inlet closing member 1702 consists of a solid ring segment shaped disc, e.g. made of polytetrafluoroethylene (PTFE) with a similar width as the upper end face 1603. For each of the chambers 1611-1618 which are covered by the inlet closing member 1702, the inlet closing member 1702 comprises a through opening 1702.1, 1702.2, 1702.3, 1702.4, 1702.5, 1702.6, 1702.7, 1702.8. In the configuration shown in FIG. 17*a*, 17*b* the through openings 1702.1-1702.8 are placed centrally above the chambers 1611-1618 so that the chambers 1611-1618 are open at the inlet side. Additionally, the inlet closing member 1702 comprises at least one opening 1740 which is located over the circular groove 1603*a* for feeding a gaseous fluid into the circular groove 1603*a*.

Likewise, below the lower end face 1602, an outlet closing member 1701 is arranged. The outlet closing member 1701 consists as well of a solid ring shaped disc, e.g. made of polytetrafluoroethylene (PTFE) with a similar shape as the inlet closing member 1702. For each of the chambers 1611-1618 which are covered by the outlet closing member 1701 (chambers 1619 and 1620 are not covered), the outlet closing member 1701 comprises a through opening 1701.1, 1701.2, . . . , 1701.8. In the configuration shown in FIG. 17*a*, the through openings 1701.1-1701.8 are placed centrally below the chambers 1611-1618 so that the chambers 1611-1618 are open at the outlet side. Additionally, the outlet closing member 1701 comprises an opening (not shown) which is located over the circular groove 1602*a* for feeding a gaseous fluid into the circular groove 1602*a*.

Additionally, the arrangement shown in FIGS. 17*a* and 17*b* comprises a removal station 1710 for retrieving analytes evaporated from a sample S1 (schematically indicated by dashed lines) in chamber 1611 and removing them from the sampling unit. The removal station 1710 comprises a gas inlet 1711 which is placed on top of inlet closing member 1702 over chamber 1611 and which is in fluid communication with through opening 1702.1. Since through opening 1702.1 is as well in fluid communication with chamber 1611, a carrier gas can be introduced into chamber 1611. Placed below the outlet closing member 1701, in the region of chamber 1611, there is a sampler outlet 1712 which is in fluid communication with through opening 1701.1.

Since through opening 1701.1 additionally is in fluid communication with chamber 1611, gaseous fluids can be retrieved from chamber 1611.

Thus, in the configuration shown in FIG. 17*a*, 17*b*, by introducing a carrier gas flow into chamber 1611 through gas inlet 1711, the analytes evaporated from sample S1 can be removed via the sampler outlet 1712. If the sampler outlet 1712 is connected to an analyte inlet of an ion molecule reactor, the analytes can directly be fed into an ion molecule reactor, e.g. an ion molecule reactor 100, 200, 300, 400, 700, 800, or 900 as described above.

At the same time, chambers 1612-1618 can be flushed with a low flow of the gaseous fluid through openings 1702.2, 1702.3, 1702.4, 1702.5, 1702.6, 1702.7, 1702.8 of the inlet closing member 1702 and through openings 1701.2, 1701.3, 1701.4, 1701.5, 1701.6, 1701.7, 1701.8 of the outlet closing member 1701.

Chambers 1619 and 1620 which are not covered by the inlet closing member 1702 and the outlet closing member 1701 in the configuration of FIG. 17a, 17b are freely accessible, e.g. for loading or unloading samples.

Additionally, the arrangement shown in FIG. 17a, 17b comprises a heating unit with a controller, a heating element and a temperature sensor temperature (not shown in FIG. 17a, 17b) for setting a predefined constant of the sample holder 1600, for example a temperature of about 130° C.

In operation, a gaseous fluid, e.g. hot air is introduced into the grooves 1620a-1620j and 1630a-1630j in order to produce an air curtain between neighbouring chambers in order to reduce cross-contaminations between samples. Thereby, the air is delivered via channels 1620a.1,1620f.1, 1630a.1, 1630f.1 in to grooves 1630a and 1630f and likewise into the other grooves.

Figure 17C:
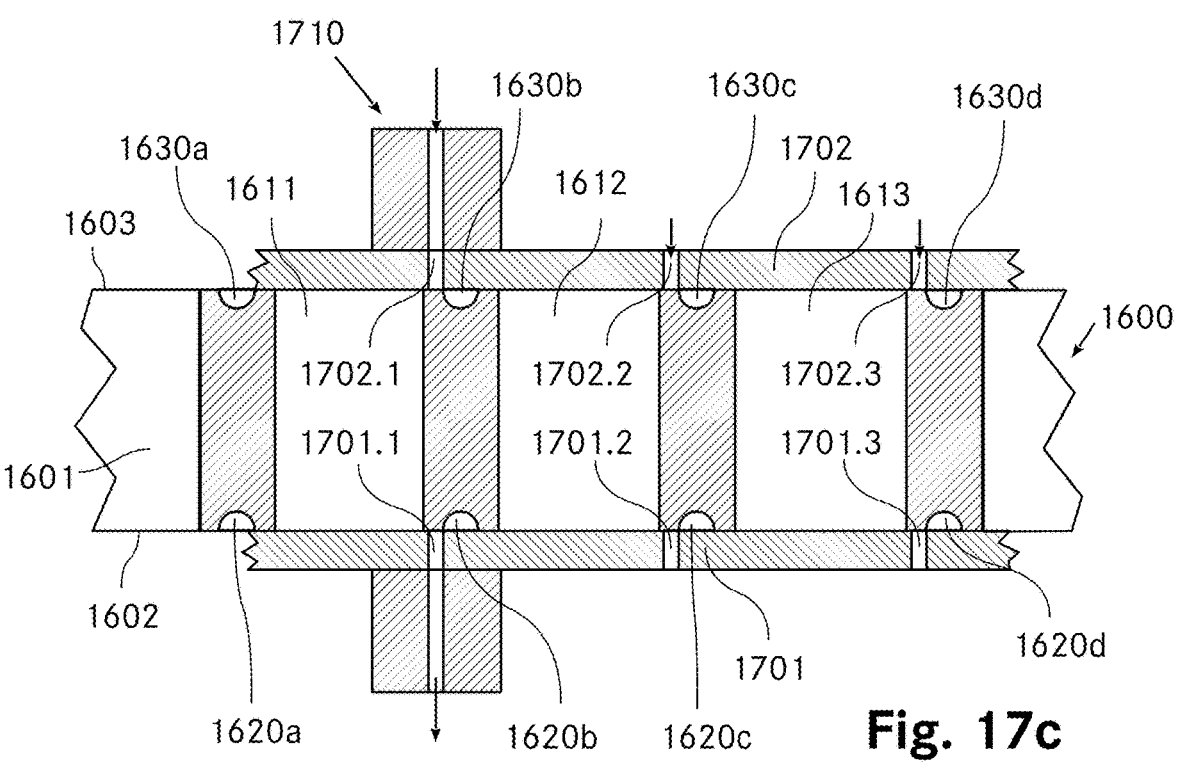
FIG. 17c The arrangement of FIG. 17b whereby the sample holder has been rotated to a position wherein the chambers are closed.

In the arrangement of FIGS. 17a and 17b, the sample holder 1600 is rotatably mounted between the inlet closing member 1702 and the outlet closing member 1701 which are fix in position. Thus, by rotation the sample holder 1600, it is possible to bring the through openings of the inlet closing member 1702 and the through openings of the outlet closing member 1701 over a section of the sample holder 1600 next to the inlet openings or next to the outlet openings, respectively, of the chambers. This situation is shown in FIG. 17c. Thus all of the chambers (e.g. chambers 1611, 1612, 1613) which are covered by the inlet closing member 1702 and the outlet closing member 1701 are closed in this situation. Thus, the sides of the inlet closing member 1702 and the outlet closing member 1701 facing the chambers (inward facing sides) can be cleaned with the air flowing through and escaping form grooves 1620a-1620f and 1630a-1630f covered by the inlet closing member 1702 and the outlet closing member 1701.

Specifically, the inward facing sides of the inlet closing member 1702 and outlet closing member 1701 are always being cleaned by the air flowing through the grooves 1630a-1630j when the sample holder 1600 is moving. The cleaning air sweeps the whole surface exposed to the sample between different samples.

Figure 17D:
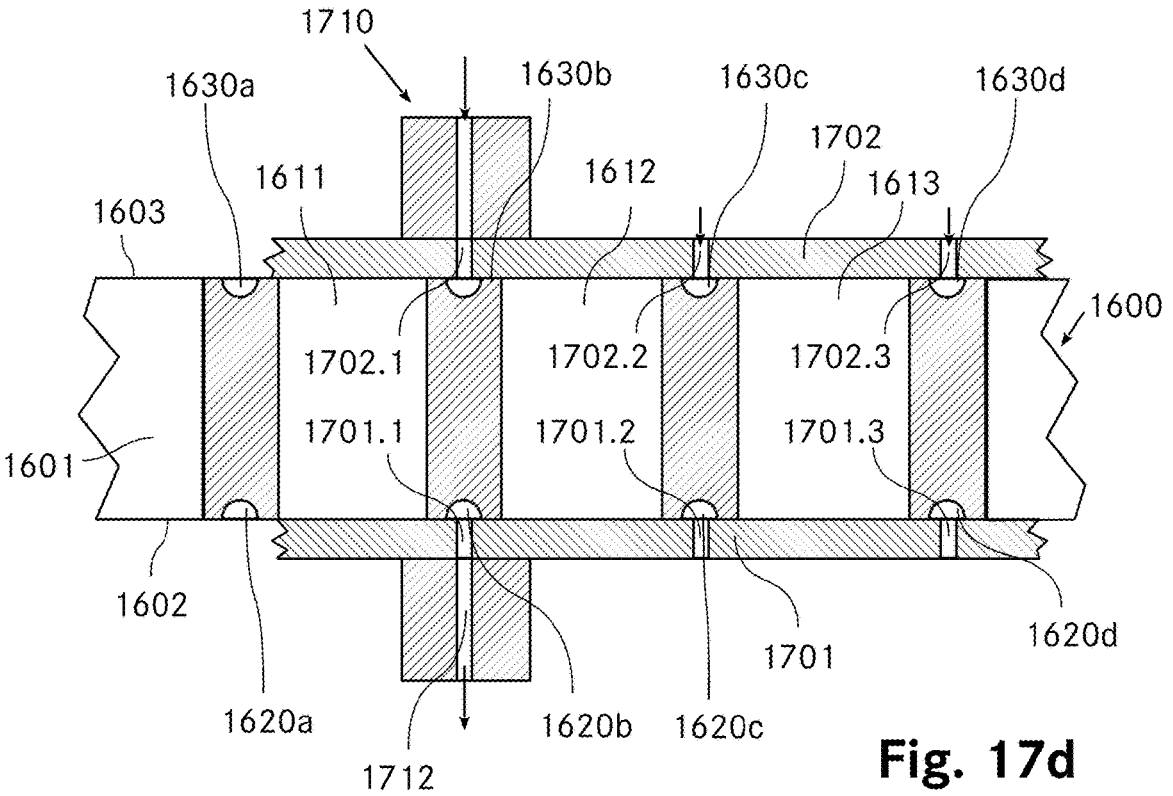
FIG. 17d The arrangement of FIG. 17b whereby the sample holder has been rotated to a position wherein the through openings of the inlet closing member and the through openings of the outlet closing member are in fluid communication with the grooves in the sample holder.

When further rotating the sample holder 1600, a position can be reached in which the through openings of the inlet closing member 1702 are in fluid communication with the grooves (e.g. 1620a-d and 1630a-d) covered by the inlet closing member 1702 or the outlet closing member 1701, respectively. This situation is shown in FIG. 17d. Thereby, the through openings (e.g. 1701.1, 1701.2, 1701.3) of the outlet closing member 1701 as well as the sampler outlet 1712 can be flushed and cleaned with gas. Additionally, this position allows for a reference measurement or zero measurement, respectively.

Figure 18:
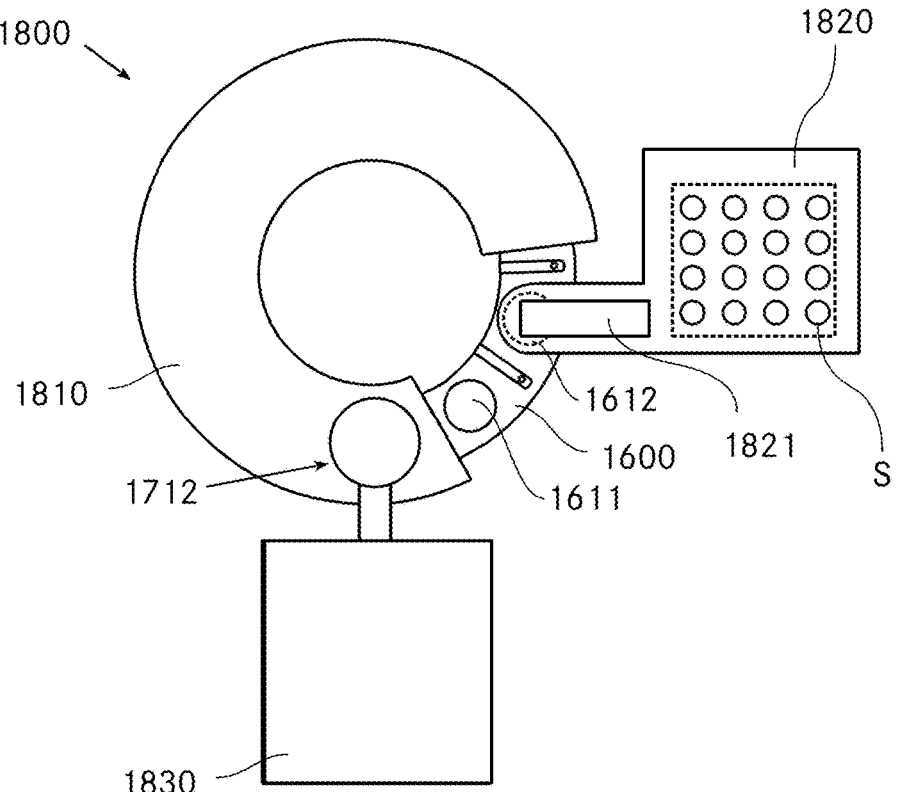
FIG. 18 A schematic view of a setup for measuring analytes from solid samples, such as cork stoppers, comprising the arrangement of FIG. 17a, preheating station, a loading unit and an ion molecular reactor.

FIG. 18 shows a schematic view of a setup 1800 for measuring analytes from solid samples such as cork stoppers. In the setup 1800, an arrangement as shown in FIG. 17a, 17b is mounted. Thereby, the inlet closing member 1702 and the outlet closing member 1701 are enclosed in a ring segment shaped housing 1810 which allows for delivering a gaseous fluid to the inlet closing member and for discharging a gaseous fluid from the outlet closing member. The sampler outlet 1712 is connected to an ion molecular reactor 1830 which is for example identical in construction with the ion molecule reactors 100, 200, 300, 400, 700, 800 or 900 as described above.

Additionally, the setup 1800 comprises a preheating station 1820 in which a plurality of samples S can be preheated to a constant temperature. The preheating station comprises a controller, a heating element and a temperature sensor (not shown) for setting the predefined constant temperature. Heating is for example effected with a hot air generating device (not shown).

The setup 1800 also comprises a loading unit 1821 for placing an individual sample S in a chamber of the sample holder and/or for removing samples from the chambers. The loading unit 1821 is placed next to a region of sample holder 1600 which is not enclosed by the housing 1810. Thus, in this region, samples can directly be introduced into the freely accessible chambers (e.g. chambers 1611 and 1612 in this configuration). By rotation of the sample holder 1600, different chambers can be loaded or unloaded sequentially.

Figure 19:
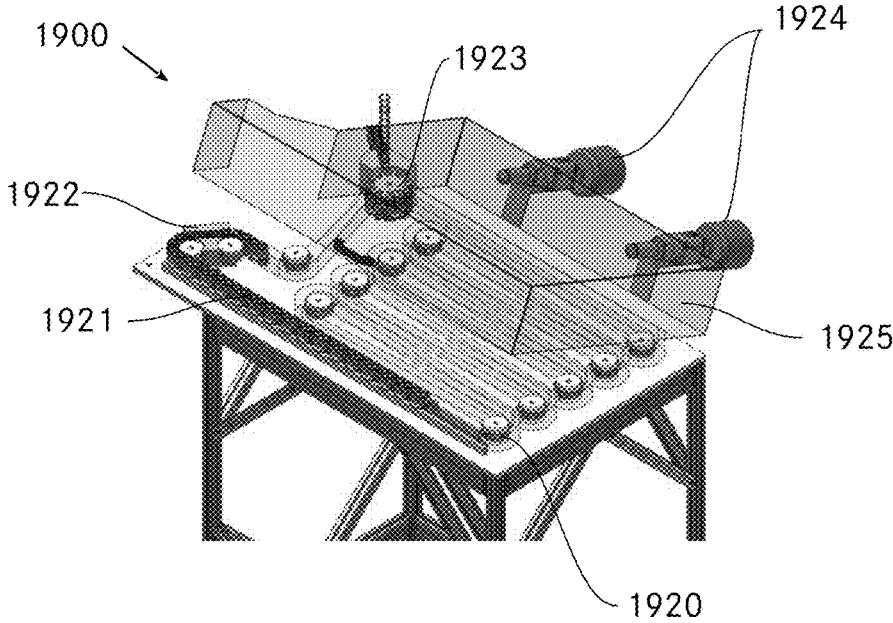
FIG. 19 A perspective view of a preheating station wherein the samples are kept in open receptacles which are part of a movable chain.

FIG. 19 shows a perspective view of a preheating station 1900 which can for example be used in the setup of FIG. 18. The preheating station 1900 comprises a snake-shaped pathway 1920 on a flat table on which a chain 1921 of interlinked and open receptacles for individual samples (see FIG. 20 for details) is movably mounted. The chain 1921 is driven by a motorized gearwheel and redirected several times with free-running gears. A feeding station 1923 allows for introducing cork samples into the receptacles. The preheating station 1900 furthermore comprises a covering 1925 which comprises two hot air generating devices 1924. If the covering 1925 is closed, hot air is flowed around the samples in the receptacles.

Additionally, a loading unit 1922 is integrated in the preheating station 1900 (see upper left-hand side in FIG. 19). In operation, the chain 1921 of interlinked and open receptacles is moved over the loading unit where at a defined position, an opening is present in the pathway 1920 of the preheating station, such that an individual sample from the receptacle located over the opening can move downwards out of the receptacle, driven by gravity. If the preheating station is properly placed over a sample holder such as e.g. shown in FIG. 18, the sample can directly be introduced into a chamber of the sample holder.

In between loading unit 1922 and feeding station 1923, the receptacles are cleaned e.g. with hot air before new cork samples are introduced. Additionally or alternatively, the receptacles can be cleaned with another gas, a liquid and/or mechanically.

Figure 20:
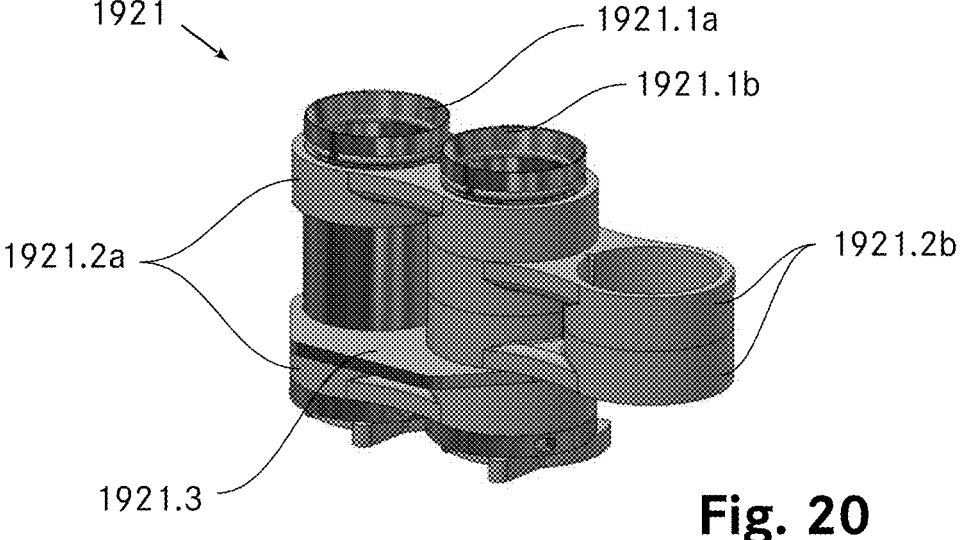
FIG. 20 A section of the moveable chain used in the preheating station of FIG. 19.

FIG. 20 shows a section of the moveable chain 1921 of FIG. 19 in detail. The moveable chain 1921 comprises a series of cylindrical pipe pieces 1921.1a, 1921.1b which are held together by a pair of outer links 1921.2a which alternate with a pair of inner links 1921.2b. Outer links 1921.2a and inner links are pivotable with respect to each other. Additionally, the chain 1921 comprises a lateral flange 1921.3 for better guiding the chain. The cylindrical pipe pieces 1921.1a, 1921.1b in which the samples, e.g. cork stoppers, are received, are open at both ends.

The preheating station 1900 can be operated in a manner synchronized to a sampling unit, e.g. the sampling unit 1700, with the help of an appropriate controller unit.

While the ion molecule reactors, mass spectrometers, samplers, arrangements, setups and methods described herein constitute preferred embodiments of this invention, it is to be understood that the invention is not limited to these embodiments, and that changes may be made therein without departing from the scope of the invention.

For example, in all of the ion molecule reactors 100, 200, 300, 400, 700, 800, 900 different and/or additional ion guides and/or electrode arrangements can be used to guide and/or focus the ions along the predefined transit paths.

For example, instead of a quadrupole setup as used in reactors 100, 200, 300 400, an octapole setup or a setup with any another number of rod electrodes can be used. Also a combined quadrupol/octapol setup can be suitable. Also, in all ion molecule reactors, e.g. additional ring electrodes can be attached inside and/or outside the housing.

In all ion molecule reactors 100, 200, 300, 400, 700 the cylindrical rod electrodes can for example be arranged within the housings. Also it is possible to use housings with electrodes integrated in the walls of the housing instead of external cylindrical rod electrodes. With ion molecule reactors 800, 900 additional ion guides in the form of multipole electrodes can e.g. be added in order to further guide the ions inside or outside the reaction volumes.

Also, the size, shapes and numbers of the electrodes described in the exemplary embodiments can be different. For example, the rod electrodes described with FIGS. 1, 2, 3, 4 and 7 can have a non-circular cross section. Moreover, the number and shape of the electrodes of the ion funnels or ion carpets described in FIGS. 3, 7, 8, 10 and 11 can be adapted if desired.

Although in the present ion molecule reactors, the pre-defined transit path is defined along a straight line along the longitudinal axis, transit paths which run along a non-longitudinal axis and/or transit paths with curved sections are possible.

Moreover, it is possible to foresee reagent ion inlets and/or reagent ion sources with other geometries. For example, in the embodiment of FIG. 2, a reagent ion inlet with ring-shaped nozzle could be used instead of the two separate inlets 230a, 230b. Also more than two separate inlets could be foreseen, e.g. 3, 4, 5, 7 or even more inlets which are preferably arranged symmetrically around the reaction volume.

Concerning the shape of the housings, non-cylindrical shapes, e.g. cuboidal shaped housing or even more complex shapes are possible as well. Specific sizes and proportions of the housings of the ion molecule reactors are not limited at all and can be adapted to specific needs if desired.

Also, the housing can be made of at least partially or fully flexible or bendable material, e.g. from plastics material. In a special embodiment, the ion molecule reactors or their housings, respectively, can be made of a bendable tube. Such a setup allows for example to effectively transfer ions over quite long distances, e.g. several meters. An embodiment with a bendable tube makes it for example possible to use the ion molecule reactor as a probe or a probe head, respectively, for taking analyte samples at random positions, e.g. similar to a vacuum cleaner.

If desired, means for heating and/or cooling can be included in the ion molecule reactors, which e.g. allow for heating and/or cooling the housings.

Also the gas permeable sections in the embodiments shown in FIGS. 3 and 4 can be used to introduce a sheath gas in order to further reduce wall effects.

Especially, in the embodiment of FIG. 3, the gas permeable section 360 can be used to introduce a sheath gas instead of removing neutrals from the reaction volume. This is an alternative approach for reducing wall effects in the ion molecule reactor. Thereby, the gas permeable section 360 can cover the whole cylindrical surface area of the housing 310 within the outer tubular element 370. In contrast to prior art systems which use a laminar flow of sheath gas with rather high pressures, the present setup results in a much lower pressure in the reaction volume.

Also, in the embodiment of FIG. 6, reagent inlets such as e.g. shown in FIG. 1 or 3 can be foreseen. In this case, instead of introducing regent ions through the gas permeable section 660, a sheath gas can be introduced into the housing 610 for reducing wall effects in the ion molecule reactor.

Moreover, the sampler 1200 shown in FIG. 12 can have a different geometry, for example it can have a cuboid container. Also it is possible to omit the encasing 1220 and to directly introduce a carrier gas 1260 via the frit ring 1214. Thereby, the carrier gas 1260 may for example be heated before with an external heater.

The container 1210 can also designed such that the complete sample, such as a cork stopper, can be taken up inside the container. Thereby, a closure might be provided in order to close the container hermetically or non-hermetically. For a non-hermetic closure, a cap with an air permeable membrane or section might be used.

Regarding the automated sampling unit 1400 of FIG. 14, it is for example possible to provide several samplers 1200 on a manipulator 1420. In this case, it is possible to pre-heat and/or analyse several samples in parallel. Thereby, it can be advantageous to use a multiport valve 1520 as shown in FIG. 15 for connecting the individual samplers with an ion molecule reactor.

Instead of the linear manipulator 1420 shown in FIG. 14, a two- or three-axis manipulator or a robotic arm can be used. Also, a circular manipulator can be used. Thereby, the conveyor belt can be omitted if desired.

Also it is possible to attach a second ion molecule reactor at the second valve outlet 1525 of the multiport valve 1520 in order to be able to measure several samples in parallel. This kind of parallel processing can help to increase the throughput further. Also, if the multiport valve has further outlets, additional ion molecule reactors can be attached.

Instead of the sample holder 1600 shown in FIG. 16a, 16b, a sample holder with more or less than 10 chambers, e.g. with 50, 75 or 100 chambers, can be used. Also, the sample holder 1600 not necessarily is of round shape. It is in principle possible to provide a straight sample holder.

The preheating station 1900 shown in FIG. 19 can be different in design as well. For example, instead or in addition to a hot air generating device, one or more heating rods can be used. Also it is possible to replace the chain 1921 by another conveying device, e.g. a conveyor band. Moreover, a manipulator can be used to take the samples out of the receptacles and/or to place them into the chambers of the sample holder. In this case, the samples can also be placed in receptacles with a closed end and/or stationary receptacles which are fixed in the preheating station.

In summary, it is to be noted that highly beneficial setups for ion molecule reactors and samplers are provided which allow for greatly increasing the efficiency of chemical ionisation and providing ionized analytes with a surprisingly high yield. In particular, due to the inventive ion molecule reactors, mass spectrometers, samplers, arrangements, set-ups and methods, it becomes possible to detect and analyse analytes with high sensitivity and allowing for a high sample throughput such as required in the detection of cork taint and/or haloanisols in cork stoppers.

The invention claimed is:

1. Ion molecule reactor for generating analyte ions from analytes, the ion molecule reactor comprising:
   a) a reaction volume in a hollow housing which reagent ions can interact with the analytes in order to form analyte ions;
   b) at least one analyte inlet for introducing the analytes along an inlet path into the reaction volume;
   c) at least one reagent ion source and/or at least one reagent ion inlet for providing reagent ions into the reaction volume;
   d) at least one ion guide comprising an electrode arrangement which is configured for producing an alternating electrical, magnetic and/or electromagnetic field, that allows for guiding the reagent ions and/or the analyte ions at least along a section of the predefined transit path through the reaction volume;

e) the at least one reagent ion source and/or the at least one reagent ion inlet comprising at least one guiding element for guiding reagent ions before entering the reaction volume;

whereby the at least one reagent ion source and/or the at least one reagent ion inlet is/are arranged coaxially around the analyte inlet and whereby the at least one reagent ion source and/or at least one reagent ion inlet and the at least one analyte inlet are located in front of the hollow housing, and configured to introduce the analytes and the reagent ions into the hollow housing along a direction running in parallel or coaxially with a longitudinal axis of the ion guide and/or the ion molecule reactor.

2. Ion molecule reactor for generating analyte ions from analytes, the ion molecule reactor comprising:

a) a reaction volume in which reagent ions can interact with the analytes in order to form analyte ions;

b) at least one analyte inlet for introducing the analytes along an inlet path into the reaction volume;

c) at least one reagent ion source and/or at least one reagent ion inlet for providing reagent ions into the reaction volume;

d) at least one ion guide comprising an electrode arrangement which is configured for producing an alternating electrical, magnetic and/or electromagnetic field, that allows for guiding the reagent ions and/or the analyte ions at least along a section of the predefined transit path through the reaction volume;

e) the ion molecule reactor further comprises a tubular element at least partially, surrounding the reaction volume, the tubular element comprising at least one porous and/or gas permeable section for removing neutrals and ions having left the predefined transit path out of the reaction volume.

3. Ion molecule reactor according to any of claim 1 or 2, whereby the at least one reagent ion source and/or the at least one reagent ion inlet is configured to produce an overall beam of reagent ions with rotational symmetry or with circular symmetry with regard to an axis defined by a direction of the first section of the transit path, the inlet path and/or the analyte inlet.

4. Ion molecule reactor according to any of claim 1 or 2, whereby the ion guide comprises an electrode arrangement with at least two electrodes, whereby the electrodes are individually addressable.

5. Ion molecule reactor according to any of claim 1 or 2, whereby the ion guide comprises a multipole electrode arrangement, an ion funnel and/or an ion carpet.

6. Ion molecule reactor according to any of claim 1 or 2, whereby reagent ions can be introduced into the reaction volume along at least two distinct directions and/or from at least two distinct positions.

7. Ion molecule reactor according to claim 1, whereby the ion molecule reactor comprises at least one porous and/or gas permeable section.

8. Ion molecule reactor according to claim 2, whereby the at least one reagent ion source and/or the at least one reagent ion inlet comprises at least one guiding element for guiding reagent ions before entering the reaction volume.

9. Ion molecule reactor according to any of claim 1 or 8, whereby the at least one guiding element produces an electrical, magnetic and/or electromagnetic field that allows for guiding the reagent ions before entering the reaction volume.

10. Ion molecule reactor according to any of claim 1 or 8, whereby the at least one guiding element comprises an electrode arrangement.

11. Ion molecule reactor according to claim 5, whereby the ion funnel comprises a stack of at least two ring electrodes whose inner diameter gradually decreases.

12. Ion molecule reactor according to any of claim 1 or 2, whereby the inlet path runs essentially along at least a first section of the predefined transit path in the reaction volume.

13. Method for generating analyte ions with an ion molecule reactor according to any of claim 1 or 2 comprising the steps of:

a) Introducing analytes into a reaction volume of a chamber of the ion molecule reactor through an analyte inlet;

b) Providing reagent ions and introducing the reagent ions into the reaction volume;

c) Letting the reagent ions interact with the analytes in order to form analyte ions;

d) Guiding the reagent ions and/or the analyte ions with an ion guide along a predefined transit path through the reaction volume.

14. Method according to claim 13, whereby the analytes are introduced into the reaction volume along an inlet path into the reaction volume whereby a direction of the inlet path runs essentially along at least a first section of the predefined transit path in the reaction volume.

15. Method according to claim 13, whereby the analytes are introduced into the reaction volume in the form of a mixture together with a plurality of further chemical species.

16. Method according to claim 15, whereby the mixture comprises or consists of vapour containing substances evaporated from cork.

17. Method according to claim 13, whereby the analytes comprise or consist of at least one compound selected from the group of 2,4,6-trichloroanisole (TCA), 2,3,4,6-tetrachloroanisole (TeCA), 2,3,4,5,6-pentachloroanisole (PCA) and 2,4,6-tribromoanisole (TBA).

18. Method according to claim 15, whereby the mixture furthermore comprises a carrier gas.

19. Method according to claim 13, whereby a pressure in the ion molecule reactor is below 500 mbar.

20. Method according to claim 13, whereby the analyte ions are generated from the analytes and the reagent ions by chemical ionisation.

21. Method according to claim 20, whereby the reagent ions are chosen such that a population of unprotonated analyte ions ($M^+$) formed is greater than a population of protonated analyte ions ($MH^+$) formed.

22. Method according to claim 13, whereby the reagent ions are chosen from $NO^+$ and/or $O_2^+$.

23. Method according to claim 13, whereby the analyte ions produced in the ion molecule reactor are introduced into a mass analyzer selected from a time-of-flight mass analyzer, a quadrupole mass analyzer, an ion trap analyzer, a sector field mass analyzer, and/or a Fourier transform ion cyclotron resonance analyzer.

*   *   *   *   *